US009272090B2

(12) United States Patent
Salinas et al.

(10) Patent No.: US 9,272,090 B2
(45) Date of Patent: *Mar. 1, 2016

(54) BURN PATIENT RESUSCITATION SYSTEM

(71) Applicants: The United States of America, as represented by the Secretary of the Army, Washington, DC (US); Board of Regents of the University of Texas System, Austin, TX (US)

(72) Inventors: Jose Salinas, San Antonio, TX (US); George C. Kramer, Galveston, TX (US); Guy A. Drew, San Antonio, TX (US)

(73) Assignees: The United States of America as represented by The Secretary of the Army, Washington, DC (US); Board of Regents of the University of Texas System, Austin, TX (US)

( * ) Notice: Subject to any disclaimer, the term of this patent is extended or adjusted under 35 U.S.C. 154(b) by 178 days.

This patent is subject to a terminal disclaimer.

(21) Appl. No.: 14/094,436

(22) Filed: Dec. 2, 2013

(65) Prior Publication Data
US 2014/0155818 A1 Jun. 5, 2014

Related U.S. Application Data

(60) Continuation of application No. 13/438,434, filed on Apr. 3, 2012, now Pat. No. 8,597,273, which is a continuation of application No. 12/977,609, filed on Dec. 23, 2010, now Pat. No. 8,157,785, which is a
(Continued)

(51) Int. Cl.
A61M 31/00 (2006.01)
B65D 81/00 (2006.01)
(Continued)

(52) U.S. Cl.
CPC .............. *A61M 5/1723* (2013.01); *A61B 5/412* (2013.01); *G06F 19/345* (2013.01); *G06F 19/3468* (2013.01); *A61B 5/20* (2013.01); *A61M 2202/0496* (2013.01)

(58) Field of Classification Search
CPC . A61B 5/20; A61B 5/412; A61M 2202/0496; A61M 5/1723; G06F 19/345; G06F 19/3468
USPC .............. 604/31, 65, 66, 131, 151, 503, 504; 600/582
See application file for complete search history.

(56) References Cited

U.S. PATENT DOCUMENTS 3,245,415 A 4/1966 Koch et al.
3,561,427 A 2/1971 Profy
(Continued)

FOREIGN PATENT DOCUMENTS

DE 199 55 368 A1 5/2001
FR 2 592 306 A1 7/1987
(Continued)

OTHER PUBLICATIONS
"CARA Pump Control Software", Feb. 2, 1999, Doc Version 2.0, Rev. 5, pp. 1-13.
(Continued)

Primary Examiner — Kevin C Sirmons
Assistant Examiner — William Carpenter
(74) Attorney, Agent, or Firm — Elizabeth Arwine

(57) ABSTRACT

A system for operating a semi-closed loop and/or a closed loop resuscitation of a burn patient in view of patient information and other physiological data gathered by the system. The system in at least one embodiment includes an urine sensor, an infusion pump and a processor that controls the operation of the infusion pump at least in part from a signal received from the urine sensor.

20 Claims, 25 Drawing Sheets

Related U.S. Application Data division of application No. 12/076,554, filed on Mar. 19, 2008, now Pat. No. 7,857,803.

(60) Provisional application No. 60/895,670, filed on Mar. 19, 2007.

(51) Int. Cl.
  *A61M 5/172* (2006.01)
  *A61B 5/00* (2006.01)
  *G06F 19/00* (2011.01)
  *A61B 5/20* (2006.01)

(56) References Cited

U.S. PATENT DOCUMENTS

| | | |
|---|---|---|
| 3,749,285 A | 7/1973 | Latham, Jr. |
| 3,999,542 A | 12/1976 | Shaw |
| 4,137,915 A | 2/1979 | Kamen |
| 4,173,224 A | 11/1979 | Marx et al. |
| 4,286,590 A * | 9/1981 | Murase ............................ 604/30 |
| 4,291,692 A | 9/1981 | Bowman et al. |
| 4,343,316 A | 8/1982 | Jespersen |
| 4,392,849 A | 7/1983 | Petre et al. |
| 4,457,751 A | 7/1984 | Rodler |
| 4,467,844 A | 8/1984 | Di Gianfilippo et al. |
| 4,494,950 A | 1/1985 | Fischell |
| 4,688,577 A | 8/1987 | Bro |
| 4,803,625 A | 2/1989 | Fu et al. |
| 4,880,014 A | 11/1989 | Zarowitz et al. |
| 4,908,350 A | 3/1990 | Kramer et al. |
| 5,002,055 A | 3/1991 | Merki et al. |
| 5,100,380 A | 3/1992 | Epstein et al. |
| 5,116,312 A | 5/1992 | Blankenship et al. |
| 5,142,484 A | 8/1992 | Kaufman et al. |
| 5,269,301 A | 12/1993 | Cohen |
| 5,298,021 A | 3/1994 | Sherer |
| 5,318,540 A | 6/1994 | Athayde et al. |
| 5,331,549 A | 7/1994 | Crawford, Jr. et al. |
| 5,352,195 A | 10/1994 | McEwen |
| 5,368,195 A | 11/1994 | Pleet et al. |
| 5,626,151 A | 5/1997 | Linden |
| 5,733,259 A | 3/1998 | Valcke et al. |
| 5,810,202 A | 9/1998 | Hoback et al. |
| 5,882,207 A | 3/1999 | Lampotang et al. |
| 6,010,454 A * | 1/2000 | Arieff et al. .................. 600/309 |
| 6,101,816 A | 8/2000 | Wang et al. |
| RE36,871 E | 9/2000 | Epstein et al. |
| 6,187,767 B1 | 2/2001 | Araneo et al. |
| 6,280,408 B1 | 8/2001 | Sipin |
| 6,682,481 B2 | 1/2004 | McKinley et al. |
| 6,690,280 B2 | 2/2004 | Citrenbaum et al. |
| 6,694,977 B1 | 2/2004 | Federowicz et al. |
| 7,402,153 B2 | 7/2008 | Steil et al. |
| 7,857,803 B1 | 12/2010 | Salinas et al. |
| 7,879,020 B1 | 2/2011 | Salinas et al. |
| 8,157,785 B2 * | 4/2012 | Salinas et al. ................. 604/503 |
| 8,409,130 B2 | 4/2013 | Sondeen et al. |
| 8,585,675 B2 | 11/2013 | Salinas et al. |
| 8,597,273 B2 * | 12/2013 | Salinas et al. ................. 604/503 |
| 2002/0029776 A1 * | 3/2002 | Blomquist ............... 128/200.11 |
| 2002/0038392 A1 | 3/2002 | De La Huerga |
| 2002/0050142 A1 | 5/2002 | Wang et al. |
| 2002/0058861 A1 | 5/2002 | Drew |
| 2002/0143290 A1 | 10/2002 | Bui et al. |
| 2003/0050621 A1 | 3/2003 | Lebel et al. |
| 2003/0207464 A1 | 11/2003 | Lemmo et al. |
| 2004/0039602 A1 * | 2/2004 | Greenberg et al. ............... 705/2 |
| 2004/0258541 A1 | 12/2004 | Glatzmaier |
| 2005/0101907 A1 | 5/2005 | Sondeen et al. |
| 2005/0108057 A1 * | 5/2005 | Cohen et al. ..................... 705/3 |
| 2005/0143671 A1 | 6/2005 | Hastings et al. |
| 2006/0052764 A1 | 3/2006 | Gelfand et al. |
| 2006/0134598 A1 | 6/2006 | Kenney |
| 2009/0018504 A1 | 1/2009 | Pile-Spellman et al. |

FOREIGN PATENT DOCUMENTS

| | | |
|---|---|---|
| FR | 2 682 602 A1 | 4/1993 |
| WO | WO 94/11054 | 5/1994 |
| WO | WO 2007/078463 A1 | 7/2007 |

OTHER PUBLICATIONS

"CARA System Architecture Specification", Apr. 5, 1999, Doc. Version 1.0, Rev. 2, p. 1.

"CARA Pump Control Software" Jun. 18, 1999, Doc Version 4.0, Rev. 10, pp. 1-6.

"CARA Simulation: Overview of the Model", Oct. 7, 2004, Computer Website Article: http://bsd7.starkhome.cs.sunysb.edu/~cara/overview.html.

"CARA Increment 1", Jul. 7, 1999, Version 4.0, pp. 1-13.

"CARA Increment 2", Mar. 6, 2000, Version 1.7, pp. 1-11.

"CARA Pump Control Software", Jan. 25, 2001, Version 6.1, Rev. 4, pp. 1-10.

"CARA Increment 3 with Questions", Feb. 5, 2002, Version 1.1, pp. 1-11.

"CARA Increment 3", Apr. 8, 2004, Version 3.0, pp. 1-11.

Abbod, M.F., et al., "Survey on the Use of Smart and Adaptive Engineering Systems in Medicine," Artificial Intelligence in Medicine, 2002, pp. 179-209, vol. 26.

Aliabadi-Wahle, S., et al., "Effects of Vitamin C on Edema Formulation at the Site of Scald Injury," Proc. Am. Burn Assoc., 1996, p. 76, vol. 28.

Arieff, Allen I., "Fatal Postoperative Pulmonary Edema: Pathogenesis and Literature Review," CHEST Journal, May 1999, pp. 1371-1377, vol. 115.

Barrow, Robert E., et al., "Early Fluid Resuscitation Improves Outcomes in Severely Burned Children," Resuscitation, Jan. 11, 2000, pp. 91-96, vol. 45.

Baxter, Charles R, et al., "Physiological Response to Crystalloid Resuscitation of Severe Burns," Annals New York Academy of Sciences, 1968, pp. 874-894, vol. 150, No. 3.

Bert, J.L., et al., "Microvascular Exchange During Burn Injury: II. Formulation and Validation of a Mathematical Model," Circulatory Shock, 1989, pp. 199-219, vol. 28.

Bert, J.L., et al., "Microvascular Exchange During Burn Injury: IV. Fluid Resuscitation Model," Circulatory Shock, 1991, pp. 285-297, vol. 34.

Bert, L., et al. "Pressure-volume Relationship for Rat Dermis: Compression Studies," Acta Physiol Scand, 1997, pp. 89-94, vol. 160.

Bowman, R. J., et al., "A Microcomputer-Based Fluid Infusion System for the Resuscitation of Burn Patients," IEEE Transactions on Biomedical Engineering, Jun. 1981, pp. 475-479, vol. BME-28, No. 6.

Brandstrup, Birgitte, et al., "Effects of Intravenous Fluid Restriction on Postoperative Complications: Comparison of Two Perioperative Fluid Regimens a Randomized Assessor-Blinded Multicenter Trial," Annals of Surgery, Nov. 2003, pp. 641-648, vol. 238, No. 5.

Brunner, Josef X., "Principles and History of Closed-Loop Controlled Ventilation," Respiratory Care Clinics of North America, Sep. 2001, pp. 341-362, vol. 7, No. 3.

Cancio, Leopoldo C., et al., "Predicting Increased Fluid Requirements During the Resuscitation of Thermally Injured Patients," The Journal of Trauma, Feb. 2004, pp. 404-414, vol. 56, No. 2.

Chaisson, Neal F., "Near-Infrared Spectroscopy-Guided Closed-Loop Resuscitation of Hemorrhage," The Journal of Trauma Injury, May 2003, pp. S183-S192, vol. 54, No. 5.

Demling, Robert H., "Pulmonary Edema: Current Concepts of Pathophysiology, Clinical Significance, and Methods of Measurements," World Journal of Surgery, Apr. 1987, pp. 147-153, vol. 11.

Elgio, Geir Ivar, et al., "Burn Resuscitation with Two Doses of 4 mL/kg Hypertonic Saline Dextran Provides Sustained Fluid Sparing: A 48-Hour Prospective Study in Conscious Sheep," The Journal of Trauma, Apr. 5, 2000, pp. 251-265, vol. 49, No. 2.

Elgio, Geir Ivar, et al., "Hypertonic Saline Dextran Produces Early (8-12 hrs) Fluid Sparing in Burn Resuscitation: A 24-hr Prospective, Double-Blind Study in Sheep," Crit Care Med, 2000, pp. 163-171, vol. 28.

(56) References Cited

OTHER PUBLICATIONS

Elgio, Geir Ivar, et al., "Resuscitation with Hypertonic Saline Dextran Improves Cardiac Function In Vivo and Ex Vivo After Burn Injury in Sheep," Shock, 1998, pp. 375-383, vol. 9, No. 5.

Engrav, L. H., et al. "A Biospy of the Use of the Baxter Formula to Resuscitate Burns or Do We Do It Like Charlie Did It?", Journal of Burn Care & Rehabilitation, Mar./Apr. 2000, pp. 91-95, vol. 21.

Hoskins, Stephen L., et al., "Closed-Loop Resuscitation of Burn Shock," Journal of Burn Care & Research, May/Jun. 2006, pp. 377-385, vol. 27, No. 3.

Ivy, Michael E., et al., "Intra-abdominal Hypertension and Abdominal Compartment Syndrome in Burn Patients," The Journal of Trauma, 2000, pp. 387-391, vol. 49.

Kramer, George, et al., "Emerging Advances in Burn Resuscitation," The Journal of Trauma, 2007, pp. S71-S72, vol. 62.

Kramer, George C., et al., "Pathophysiology of Burn Shock and Burn Edema," Herndon DN, ed., Total Burn Care, 2nd ed., New York: W.B. Saunders Company Ltd., 2002, pp. 78-87.

Lee, Insup, "Case Study: Computer Assisted Resuscitation Algorithm (CARA) System", Department of Computer and Information Science University of Pennsylvania, Jun. 22, 2001, pp. 1-26.

Lowell, Jeffrey A., et al., "Postoperative Fluid Overload: Not a Benign Problem," Critical Care Medicine, 1990, pp. 728-733, vol. 18.

Murray, Michael J., et al., "Critical Care Medicine: Perioperative Management", 2002, Lippincott Williams & Wilkins, Second Edition, p. 803-804.

Poli De Figueiredo, et al., "Hypertonic Acetate-ααHemoglobin for Small Volume Resuscitation of Hemorrhagic Shock," Art. Cells, Blood Subs., and Immob. Biotech., 1997 pp. 61-73, vol. 25.

Pruitt, Jr., Basil A., et al., "Fluid and Electrolyte Replacement in the Burned Patient," Surgical Clinics of North America, Dec. 1978, pp. 1291-1312, vol. 58, No. 6.

Pruitt, Basil Jr., "Protection of Excessive Resuscitation: 'Pushing the Pendulum Back'," The Journal of Trauma, 2000, pp. 567-568, vol. 18.

Rafie, Abraham D., et al., "Hypotensive Resuscitation of Multiple Hemorrhages Using Crystalloid and Colloids," Shock, Sep. 2004, pp. 262-269, vol. 22 No. 3.

Roa, Laura M., et al., "Analysis of Burn Injury by Digital Simulation," Burns, 1988, pp. 201-209, vol. 14, No. 3.

Salinas, J., et al., "A Fluid Balance Monitor for Enhancing Burn Resuscitation," Journal of Burn Care Res., 2007, p. S102, vol. 28.

Shah, A., "Meta-Analysis of Fluid Requirements for Burn Injury 1980-2002," Journal of Burn Care Rehabilitation, 2003, p. S118, vol. 24.

Sondeen, Jill L., et al. "Hypotensive Resuscitation in a Model of Uncontrolled Hemorrhage in Swine," presentation at ATACCC 2002, 2002, slides 1-33.

Warden, Glenn D., "Fluid Resuscitation and Early Management," Herndon DN, ed. Total Burn Care. 2nd ed. London U.K.: Saunders, 2007, pp. 107-118.

Westenskow, Dwayne R., Ph.D. et al., "Microprocessors in Intensive Care Medicine," Medical Instrumentation, Nov.-Dec. 1980, pp. 311-313, vol. 14, No. 6.

Wolf, Steven E., et al. "Mortality Determinants in Massive Pediatric Burns," Annals of Sugery, 1997 pp. 554-569, vol. 225, No. 5.

Wysocki, Marc, et al., "Closed-Loop Ventilation: An Emerging Standard of Care?," Critical Care Clinics, 2007, pp. 223-240, vol. 23.

Ying, Hao, et al., "Fuzzy Control of Mean Arterial Pressure in Post-surgical Patients with Sodium Nitroprusside Infusion," Oct. 1992, pp. 1060-1070, vol. 39, No. 10.

\* cited by examiner

BURN PATIENT RESUSCITATION SYSTEM

This application is a continuation application of U.S. patent application Ser. No. 13/438,434, filed on Apr. 3, 2012 and now is U.S. Pat. No. 8,597,273, which is a continuation application of U.S. patent application Ser. No. 12/977,609, filed on Dec. 23, 2010 and now is U.S. Pat. No. 8,157,785, which is a divisional application of U.S. patent application Ser. No. 12/076,554, field on Mar. 19, 2008 and now is U.S. Pat. No. 7,857,803, which claims the benefit of U.S. provisional application Ser. No. 60/895,670, filed on Mar. 19, 2007 entitled Approaches to Improving Treatment of Burn Patients. These applications are hereby incorporated by reference.

The U.S. Government in addition to any other rights it may have through at least one inventor has a paid-up license in this invention and the right in limited circumstances to require the patent owner to license others on reasonable terms as provided for by the terms of award number N00014-03-1-0363 awarded by the Office of Naval Research, Department of Defense.

I. FIELD OF THE INVENTION

This invention relates to a semi-closed loop or closed loop system and method for burn patient resuscitation.

II. BACKGROUND OF THE INVENTION

Effective resuscitation of burn injuries is critical for lowering both the mortality and morbidity rates of burn patients. Both treatment and rehabilitation of burn injuries requires a large economic investment by hospitals in terms of cost and long term intensive care requirements for patients with severe and/or large percentage body burns. It is not uncommon that a normal size adult will receive over 30 liters of fluid while having urinary output (or urine output) totaling less than 2 liters, which results in a gain of about 60 pounds from the fluid retention in the body resulting from, for example, capillary leakage in response to the injury.

Each year approximately 45,000 adults and 15,000 children require hospitalization due to burn injury with 5,000 dying due to the severity or complications resulting from their injuries. For the military population, injury patterns due to current conflicts may include both traumatic and burn injuries that necessitate immediate treatment. Furthermore, recent studies have shown that over resuscitation of burn injury is not uncommon, resulting in significant iatrogenic complications.

Critical to survival are the initial 48 hours of post-burn resuscitation; however, this time period is extended in situations where the patient takes a long time for care and eventual transport such as occurs when brining burned soldiers from the Iraq theater to the U.S. Army Institute of Surgical Research (USAISR) burn unit at Fort Sam Houston, Tex. During this phase, patients require prompt initiation of fluid therapy, and around-the-clock care by experienced burn surgeons and intensivists. However, advanced burn care expertise is not found in most hospitals, and the care outside of burn centers can lead to increase morbidity from infusing too much fluid. This limitation includes receiving centers, whether they are civilian emergency rooms, forward military facilities or ad hoc medical facilities for mass casualty. Because acute burn care is particularly labor intensive, burn injuries sustained in mass casualties can quickly overwhelm even the best hospitals and burn centers. Clearly, there is a need to reduce the workload of advanced burn centers and to impart burn expertise to less specialized medical facilities.

The pathophysiologic response to large thermal injuries ($\geq 30\%$ of total body surface area [TBSA]) is characterized by substantial plasma extravasation and general edema formation, leading to intravascular volume depletion and burn shock. Delayed or inadequate fluid resuscitation is associated with increased morbidity and mortality. Initial treatment currently consists of isotonic crystalloid infusion based on a regimen that is directed towards volume replenishment to obtain cardiovascular stabilization and maintain adequate renal function. However, such treatment is only partially effective due to an array of circulatory mediators and sustained fluid extravasations into the extravascular space.

a. Current Resuscitation Regimens

Defining the best solutions, infusion rates, and volume requirements for resuscitation of burn injury has been an ongoing research focus for the last 100 years. Several formulas have been developed to guide the care provider with a predicted infusion volume for the first 24 hours and with a specific initial infusion rate based on the size of the burn injury and patient weight. Infusion rates are adjusted hourly, based on the urinary output (UO) of the patient during the last measured period. The most common contemporary infusion formulas are the Brooke formula (2 ml/kg per % TBSA for 24 hours) and the Parkland formula (4 ml/kg per % TBSA for 24 hours). Fluids are periodically adjusted to maintain an adequate urinary output, within a predetermined target range. The rationale for using urinary output as the target endpoint to adjust fluid therapy is that if urinary output is normal then glomerular filtration rate, renal blood flow, and cardiac output are likely to be adequate. Target values are based on ranges determined by age (adult or pediatric), patient weight, and sometimes other factors that contribute to normal renal output. Adult target values are 0.5-1.0 ml/kg per hour or 30-50 ml/hr. Pediatric patients often require larger volumes due to greater insensible losses, and have a formula with a higher target urinary output of 1.0-2.0 ml/kg per hr. Maintaining urinary output targets is expected to normalize renal function, while avoiding excess or inadequate fluid infusion that may lead to an increase in complications or mortality. But recent reviews have suggested that this approach frequently leads to severe over-resuscitation, with many burn units administering mean volumes larger than the Parkland recommendation.

The current standard of care for patients receiving burn resuscitation is paper charts that include a flow sheet similar to that illustrated in FIG. 1A. In some situations where electronic charting is used, the monitors will provide data to the electronic charting system as illustrated in FIG. 1B, which is only a slight improvement over the flow sheet since there is no analysis of the data.

To evaluate contemporary methods of burn resuscitation, a meta-analysis of the last 26 years of burn resuscitation was conducted. A search of Medline for all clinical burn studies in which fluid resuscitation was guided by the Brooke or Parkland formula with adjustment in infusion rates to restore and maintain target urinary output was done. Data from 31 studies, which included 40 groups and 1,498 patients was extracted. FIGS. 2A and 2B show the total 24-hr volumes infused and the mean urinary outputs, respectively. Mean percentage of total body surface area (% TBSA) was $45\pm 2\%$ and mean fluid intakes were $5.1\pm 1.3$ mL/kg per % TBSA, with mean 24-hr urinary outputs of $1.1\pm 0.4$ mL/hr per kg. All studies reported mean volume administration exceeding the Brooke formula and 86% of studies reported mean values above the Parkland formula. In general, patients are resuscitated to achieve levels of urinary output that are at or above the high end of target level. However, most of the burn centers infused sufficient lactated Ringer's solution (LR) to induce mean 24-hour urinary outputs exceeding 1.0 mL/kg. The primary conclusions from the meta-analysis are: (1) total volumes infused typically exceed the Parkland formula and Advanced Burn Life Support (ABLS) guidelines, and (2) urinary outputs tend to be on the high side of ABLS guidelines.

The meta-analysis did not determine if burn centers are infusing more fluid than is optimal or if the Brooke and Parkland burn formulas specify inadequate volumes. A meta-analysis based on summary statistics of individual studies has limited power to determine relationships between fluid volumes and outcomes. Detailed individual patient data are needed to accurately determine the impact of fluid therapy on outcomes. Individual patient data is required to statistically correlate outcomes with total volumes infused and net volume retained (in minus out). Hourly data on infusion rates, urinary output and net volume (edema) is needed to fully define the relationships between volume therapy and urinary output in burn patients.

Reduced survival and more often increased morbidity are linked to sub-optimal resuscitation. But it is unknown how many patients are harmed by under- and over-resuscitation. From the meta-analysis, case reports, and clinical experience we know that individual burn experts resuscitate patients differently and that they usually produce clinical results deemed satisfactory. This may speak more to the physiological reserves of the patients and the ability of their kidneys to compensate for over-resuscitation than it does to our medical knowledge or expertise. A quip often used by intensivists is "the dumbest kidney knows more than the smartest intern." Patients have effective compensatory mechanisms that can often compensate for a wide range of infused volumes. "Successful clinical results," however, are not necessarily equivalent to optimal outcomes.

b. Fluid Creep

The need for large volume therapy for burn shock was identified in 1968 by Charles Baxter, who showed that successful resuscitation could be accomplished with a "Parkland formula" of 4-ml/kg per % TBSA of lactated Ringer's solution in the first 24 hours of care. Baxter C R, et al., *Physiological response to crystalloid resuscitation of severe burns*, Annals of the New York Academy of Sciences, 1968, vol. 150, pp. 874-894. Prior to that time, fluid therapy was largely performed with plasma and albumin solutions at lower volume totals. Subsequently, Pruitt et al. provided an alternate "Brooke formula" of 2-ml/kg per % TBSA. Pruitt B A Jr., *Fluid and electrolyte replacement in the burned patient*, Surg Clin N Am., 1978, vol. 48, pp. 1291-1312. The Advanced Burn Care Life Support (ABLS) guidelines established by the American Burn Association accepted these formulas and recommend a 2-4 mL/kg per % TBSA range of total fluid volumes for the first 24 hours, with the infusion rate adjusted to maintain a urinary output of between 0.5 mL/kg and 1.0 mL/kg per hr or about 30-50 ml/hr. American Burn Association, *Advanced Burn Life Support Course (ABLS), Instructor's Manual*, 2001. Nevertheless, burn centers routinely administer 25-50% more fluid than the Parkland formula recommends, and more than half the fluid is given within the first 8 hours. In clinical settings, physicians may accept high urinary outputs without decreasing infusion rates and more diligently increase infusion rates when urinary output is low. This viewpoint is supported by meta-analysis, which showed that mean urinary outputs and infused volumes were typically above ABLS guidelines.

The term "fluid creep" was first used by Pruitt to describe the increased volume of fluid that appears to be administered by burn centers in the first 24-48 post-burn hours. The morbidities associated with fluid overload include pulmonary edema and impaired gas exchange, abdominal compartment and intestinal ischemia syndromes, delayed wound healing, increased incidents of infection and sepsis, and multi-organ failure. Data supports benefits of reducing total infused volumes. Recently, perioperative and ICU trials of restricted fluid therapy showed improved outcomes. Brandstrup B et al., *Effects of intravenous fluid restriction on postoperative complications: comparison of two perioperative fluid regimens: a randomized assessor-blinded multicenter trial*, Annals of Surgery, 2003, vol. 238, pp. 641-648. Less net fluid accumulation has been associated with better outcomes in large burns treated with lactated Ringer's solution (LR). Cancio L C, *Predicting Increased Fluid Requirements During the Resuscitation of Thermally Injured Patients*, The Journal of Trauma, February 2004, vol. 56, No. 2, pp. 404-413. However, the correlation between increased survival and reduced fluid also reflects that the injury level correlates morbidity and mortality, and that more severely burned patients require more fluid.

Taken together the above findings suggest that optimal fluid resuscitation may be achieved by minimizing fluid accumulation, while maintaining adequate urinary output and cardiac output. However, the clinical consequences of more tightly controlled fluid therapy and urinary output to fall within established guidelines with less hourly variations are unknown.

c. Fluid Therapy Using Closed Loop Control

The concept of closed loop control is well established for industrial applications and its potential application to medicine has been extensively reviewed, although it has had limited utilization. Abbod M F, *Survey on the use of smart and adaptive engineering systems in medicine*, Artificial Intelligence in Medicine, 2002, vol. 26, pp. 179-209; Westenskow D R, *Microprocessors in intensive care medicine*, Medical Instrumentation, November-December 1980, vol. 14, no. 6, pp. 311-313. There have been clinical trials demonstrating effective closed loop control of nitroprusside infusion for postoperative blood pressure regulation in cardiac patients. Ying H, *Fuzzy control of mean arterial pressure in postsurgical patients with sodium nitroprusside infusion*, IEEE Transactions on Biomedical Engineering, 1992, vol. 39, pp. 1060-1070. Closed loop control of ventilators and delivery of anesthetics have evolved into commercially viable products. Brunner J X, *Principles and history of closed-loop controlled ventilation*, Respiratory Care Clinics of North America, 2001, vol. 7, pp. 341-362, vii; Wysocki M et al., *Closed-loop ventilation: an emerging standard of care?*, Critical Care Clinics, 2007, vol. 23, pp. 223-240, ix. Experimentally, closed loop fluid resuscitation has been used for treatment of hemorrhaged sheep using blood pressure, cardiac output, and tissue oxygen as endpoints. Chaisson N F et al., *Near-Infrared Spectroscopy-Guided Closed-Loop Resuscitation of Hemorrhage*, The Journal of Trauma, 2003, vol. 54, no. 5, pp. S182-S192; Rafie A D et al., *Hypotensive resuscitation of multiple hemorrhages using crystalloid and colloids*, Shock, 2004, vol. 22, pp. 262-269.

Bowman and Westenskow were the first to build a closed loop controller (using a proportional-integral-derivative (PID) algorithm) for fluid resuscitation of burn injury. Bowman et al., "A Microcomputer-Based Fluid Infusion System for the Resuscitation of Burn Patients," IEEE Transactions on Biomedical Engineering, Vol. BM-28, No. 6, June 1981, pp. 475-479. In an era before personal computers were common, they built a specialized microprocessor for their controller. Both intake and urinary output were monitored with drop counters while a roller infusion pump was controlled with the PID algorithm. The PID algorithm was based on a mathematical model, which had been used to control resuscitation in a small number of dog experiments. They verified accurate monitoring of fluid in and urine out, but no control trials were performed in either animals or patients. Several decision trees and mathematical models of fluid balance after burn injury have been developed, but none has had significant clinical application. Bert J L et al., *Microvascular exchange during burn injury: II. Formulation and validation of a mathematical model*, Circulatory Shock, 1989, vol. 28, pp. 199-219; Bert J L et al., *Microvascular Exchange During Burn Injury: IV. Fluid Resuscitation Model*, Circulatory Shock, 1991, vol. 34, pp. 285-297; Roa L M et al., *Analysis of burn injury by digital simulation*, Burns Including Thermal Injuries, 1988, vol. 14, pp. 201-209.

An evaluation of individual hourly records of burn patients was done in order to define a current standard of care for burn resuscitation. Hourly fluid input and urinary output measurements from 20 adult burn patients were extracted from U.S. Army Institute of Surgical Research (USAISR) and University of Texas Medical Branch (UTMB) burn unit records. The data shown in FIG. 3 suggests great variability in urinary outputs before and after arrival at these two burn centers. Of 403 hourly in-hospital measurements in burn patients, 41% were below the ABLS target range of 1.0-2.0 mL/kg and 28% were above.

The principle conclusions from the analysis of these patients and of the literature meta-analysis are that mean urinary output above target levels predominated with infused volumes, even in advanced burn centers, exceeding ABLS guidelines. The tendency for clinicians to over-resuscitate burn patients may be responsible for many recognized complications such as abdominal compartment syndrome, extremity compartment syndrome, and airway edema requiring intubation, all of which are life- and/or limb-threatening. In particular, abdominal compartment syndrome was largely unheard before ten years ago, but is now a serious complication in many burn centers that results almost always in death.

III. SUMMARY OF THE INVENTION

Effective resuscitation is critical in reducing mortality and morbidity rates of acute burn patients. Specific closed loop system using computer-controlled feedback technology that supplies automatic control of infusion rates using decision assist guidelines can potentially achieve better control of urinary outputs. Because the system can self-adjust based on monitoring inputs, the technology can be pushed to environments such as combat zones where burn resuscitation expertise is limited. A closed loop system can also assist in the management of mass casualties, another scenario in which medical expertise is often in short supply.

The invention in at least one embodiment uses an expectant rate model to determine infusion rate based on urinary output with the expectant rate model based on how patients from a reviewed pool responded to resuscitation with fine-tuning for any one patient done to bring the patient into a desired urinary output range.

A systematic means for adjusting infusion rate using either decision assist algorithm or autonomous closed loop control may improve outcomes in patients requiring large volume fluid therapy.

Closed loop resuscitation systems can provide physicians, nurses, and other medical personnel who have limited burn experience a means to optimize the first 24 to 48 hours of burn care, even in an initial care facility. Although the invention can be used for more than 48 hours. In the prehospital mass casualties environment, or in advanced burn centers such systems could be labor saving.

At least one embodiment provides for continuous monitoring and application of control algorithms to achieve and maintain urinary output target levels better than human intervention. This critical ability to tightly manage fluid balance is due to the closed loop system's ability to continuously monitor, and rapidly interpret and respond to minute systemic changes using the application of consistent rules. A closed loop controller can adjust fluid infusions at least as well as typical clinical burn care teams. This in itself will be useful. Animal studies suggest that tighter control of urinary output may lower total volume infused and total net fluid balance. However, even if such systems yield outcomes no better than that of advance burn centers, the technology would allow expertise to be "exported" to other hospitals and trauma care facilities that do not have expertise or experience in burn care.

The invention in at least one embodiment includes a system for use in resuscitating a patient that operates as a semi-closed loop system, a closed loop system, or a combination of the two. The system includes a urine sensor; an infusion pump; and a processor connected to said urine sensor and said infusion pump, said processor having means for calculating an infusion rate based on at least the current infusion rate, the current urinary output, infusion rate model based constants, the patient's weight, the percentage of total body surface area, and a Gaussian function centered on a target urinary output, and means for controlling operation of said infusion pump based on the calculated infusion rate.

The invention in at least one embodiment includes a method for controlling the operation of a resuscitation system used to resuscitate a burn patient. The method includes receiving patient data including percentage of total body surface area; calculating an initial infusion rate based on at least the patient data; outputting the initial infusion rate to an infusion pump; obtaining a current urinary output from a sensor monitoring urinary output; calculating a new infusion rate based on at least the current infusion rate, the current urinary output, an infusion rate constant, an urinary constant; and outputting the new infusion rate to the infusion pump.

The invention in at least one embodiment includes a system for use in resuscitating a patient where the system includes: a urine sensor; an infusion pump; and a processor connected to the urine sensor and the infusion pump, the processor having means for calculating an infusion rate using an infusion rate model based on at least a current infusion rate, a current urinary output, and infusion rate model based constants, the new infusion rate is calculated using the following equation $$I_t = I_{t-1} + e(t) \times \frac{IRC_t}{UOC_t}$$

where $I_t$ is the new infusion rate, $I_{t-1}$ is the last infusion rate, $e(t)$ is the urinary output error between the current urinary output and a target urinary output, $IRC_t$ is the infusion rate constant at time t based on the hours post burn, and $UOC_t$ is the urinary constant, and means for controlling operation of the infusion pump based on the calculated infusion rate.

The invention in at least one embodiment includes a system for use in resuscitating a patient where the system includes: a urine sensor; an infusion pump; a timer; and a processor connected to the urine sensor, the infusion pump, and the timer, the processor having means for calculating an infusion rate based on at least the current infusion rate, the current urinary output, infusion rate model based constants, the patient's weight, the percentage of total body surface area, and a Gaussian function centered on a target urinary output, and means for controlling operation of the infusion pump based on the calculated infusion rate.

The invention in at least one embodiment includes a system for use in resuscitating a patient where the system includes: a urine sensor; an infusion pump; receiving means for receiving patient data including percentage of total body surface area burned and time since the patient was burned; first means for calculating an initial infusion rate based on at least the received patient data; second means for calculating an urinary output error based on a difference between a target urinary output and a current urinary output provided by the urine sensor; third means for calculating a new infusion rate based on at least the calculated urinary output error multiplied by a constant calculated in part based on an exponential function with the input of hours post burn for the patient with the result being added to the current infusion rate; outputting means for outputting the new infusion rate to the infusion pump; and a timer for controlling the operation of the second means, the third means and the outputting means.

Given the following enabling description of the drawings, the apparatus should become evident to a person of ordinary skill in the art.

IV. BRIEF DESCRIPTION OF THE DRAWINGS

In some of the figures in the patent application, certain information has been redacted to remove identification of any patients from or has replace identifying information with non-descript information in the illustrated interfaces The present invention is described with reference to the accompanying drawings. In the drawings, like reference numbers indicate identical or functionally similar elements. The use of cross-hatching and shading within the drawings is not intended as limiting the type of materials that may be used to manufacture the invention.

Figure 1A:
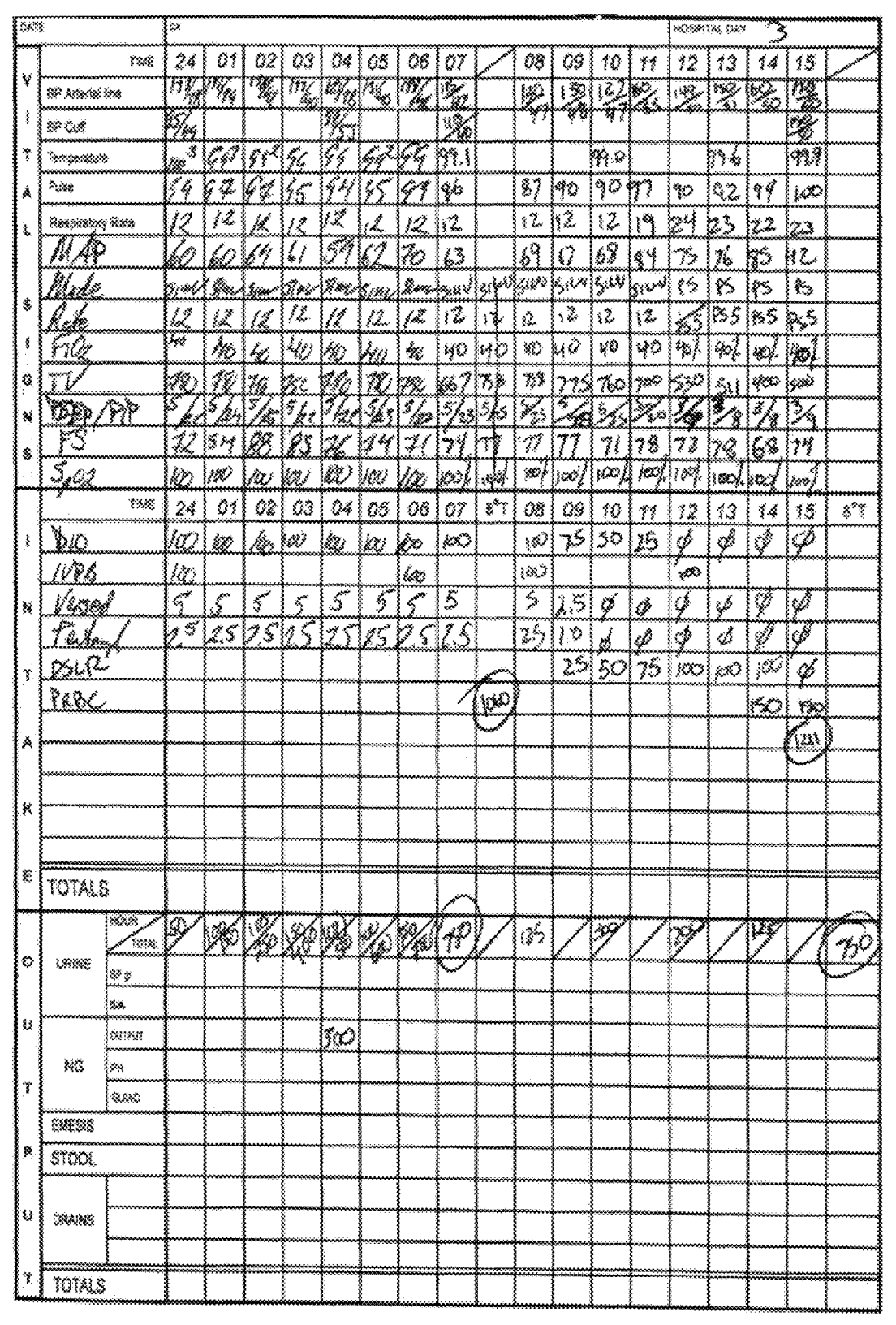
Figure 1B:
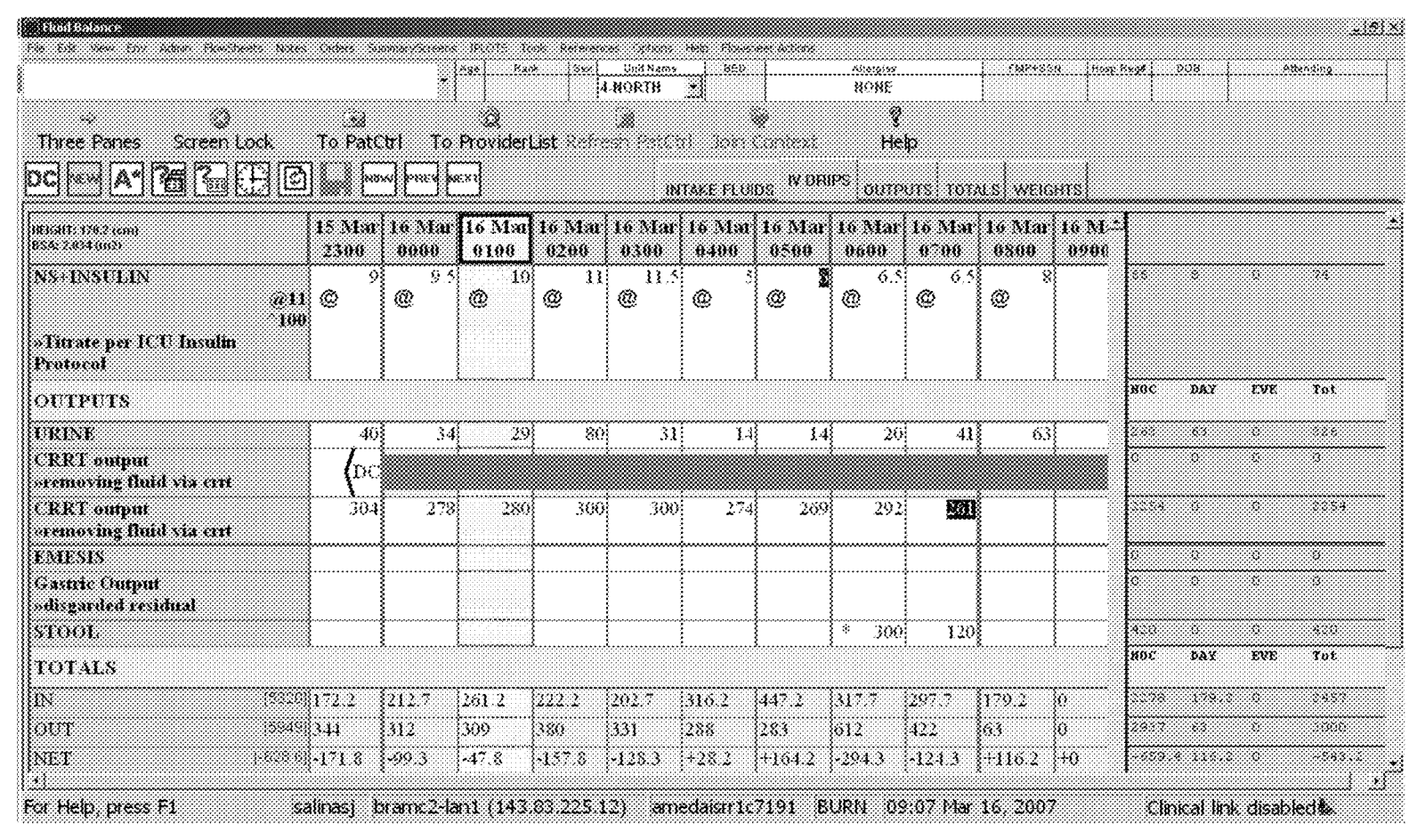

FIGS. 1A and 1B illustrate the current records being used in the burn centers.

V. DETAILED DESCRIPTION OF THE DRAWINGS

Figure 2A:
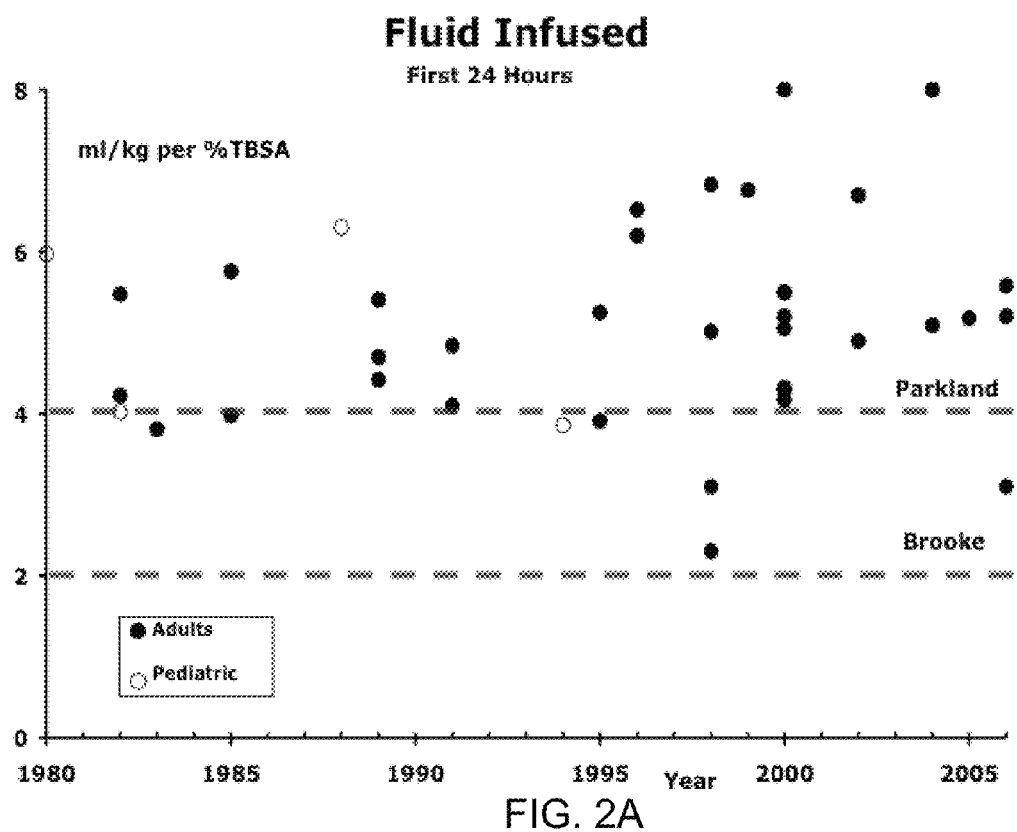
FIGS. 2A and 2B depict data regarding fluid infused and urinary output obtained from a retroactive study.
Figure 2B:
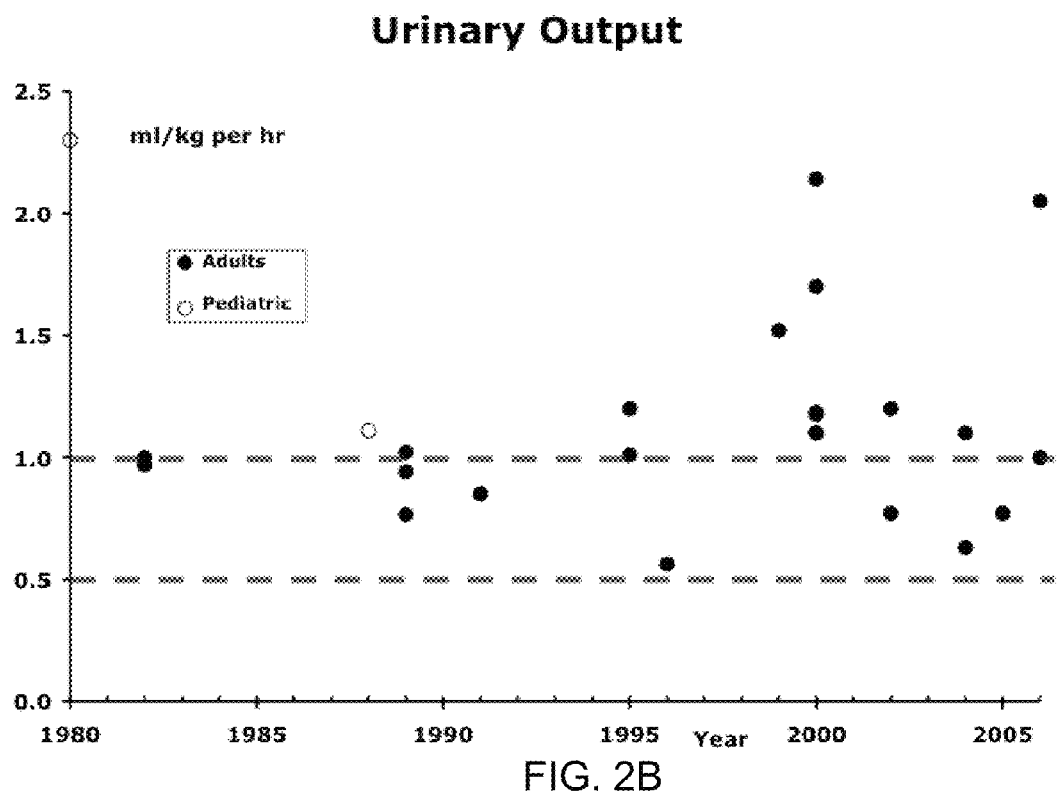
Figure 3:
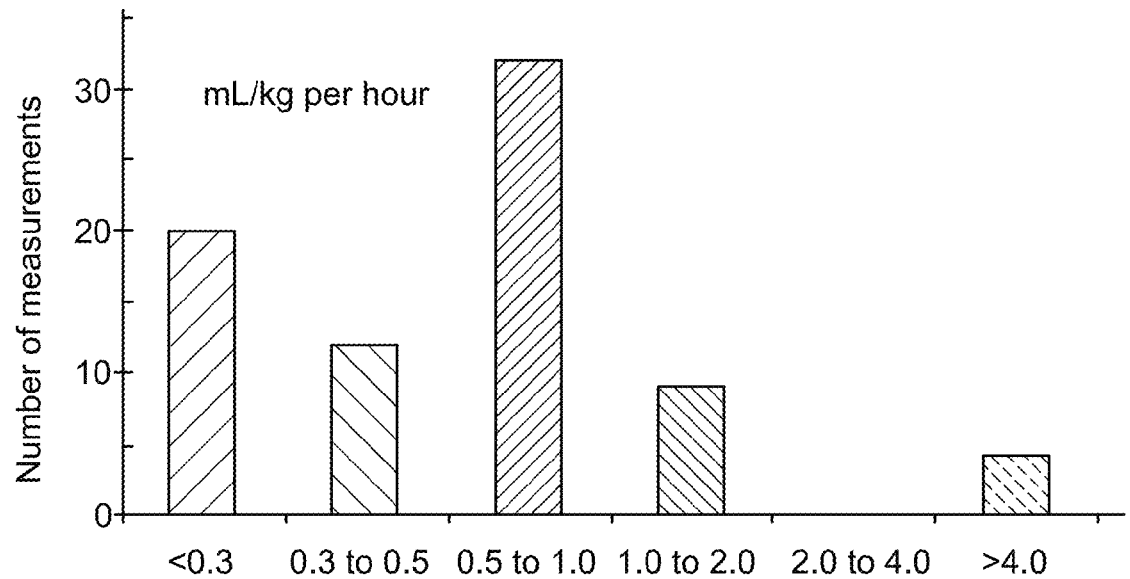
FIG. 3 illustrates the number of urinary output measurements and where they fell along a spectrum from medical records at UTMB and USAISR.
Figure 3:
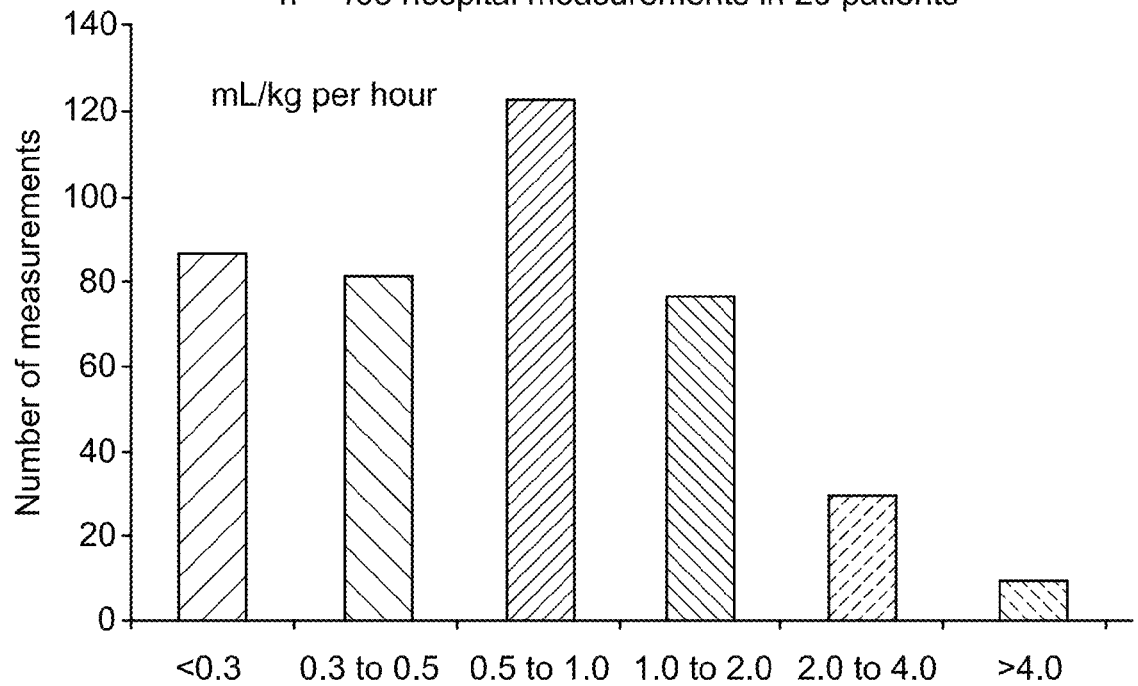

The invention includes a method for providing controlling the infusion rates of a semi-closed loop system or a closed-loop system to achieve a target urinary output using model based infusion constants. Urinary output is a surrogate marker for renal blood flow, adequate resuscitation and adequate cardiovascular function, but does not require an invasive procedure to be able to monitor blood flow to be able to monitor cardiovascular function. The system was developed based in part on a retrospective analysis of 30 burn patients at the USAISR burn ward that had greater than 20% TBSA. The retrospective analysis will be discussed later in this specification.

The invention also includes a system capable of performing and/or implementing the method, and an example of a system is discussed in connection with FIGS. 10A-10F and 15A-18. The semi-closed-loop system and the closed-loop system use a compensation model will make a decision on the level of titration that can be used in conjunction with a urine meter (or sensor) to receive urinary output data and an infusion pump to set the infusion rate. In such an arrangement, the system can make adjustments more frequently than occurs with human oversight. The frequency at which sampling can occur in such an arrangement is limited by the accuracy of the urinary output meter and physiology; however, standard filtering can be used to reduce noise and counteract these limitations.

A semi-closed loop system is one in which the recommendation for the infusion rate is provided to the medical staff for their approval (or acceptance) before the infusion rate is used by the system. In at least one embodiment, upon expiration of a predetermined time limit with no response from the medical staff, the recommended infusion rate is used by the system. In some embodiments, the semi-closed loop system will receive a different infusion rate from the medical staff then that recommended to be used. In contrast, a closed loop system will operate independent of interaction with the medical staff, although in some embodiments the system will provide information related to the resuscitation to allow for oversight by the medical staff and/or allow for the medical staff to terminate the resuscitation if needed. Both systems are able to utilize the following described method for controlling the calculation of the infusion rate that governs a particular burn resuscitation. In at least one embodiment, the user is able to select whether the system will operate as a semi-closed loop system or as a closed loop system.

The recommendations provided by the invention are based at least on the urinary output of the patient, infusion rate given to the patient, and hours post burn (HPB). In some embodiments, the recommendations are based also on at least one of patient weight and percentage of total body surface area (TBSA). In some embodiments, the recommendations are based also on at least the length of time of a certain physiological condition. An example of a system that can provide the information to the method is an infusion pump and a flow meter measuring the amount of urine collected through a catheter.

An example of a base infusion rate calculation that can be used in the method and by the system is $$I_t = I_{t-1} + e(t) \times \frac{IRC_t}{UOC_t} \tag{1A}$$

where $I_t$ is the new infusion rate, $I_{t-1}$ is the last infusion rate, $e(t)$ is the urinary output error, $IRC_t$ is the infusion rate constant at time t based on the hours post burn, and $UOC_t$ is the urinary constant. Based on data analysis sampled from clinical records of thirty burn patients, $UOC_t$ is set at 1.211. Equation (1) defines the new infusion rate based on the mean model values found through recursive study of burn resuscitation data. The infusion rate constant and urinary constant are model based constants derived from data analysis of clinical records of burn patients.

Equation (1) can be adjusted to reflect that not all patients have the same weight and/or total body surface area. As such Equation (1) in at least one embodiment is modified to include at least one of a weight modifier ($Y_{weight}$) or a total body surface area modifier ($Y_{tbsa}$) as illustrated in Equation (1B) that includes both modifiers:

$$I_t = I_{t-1} + e(t) \times \frac{IRC_t}{UOC_t} \times Y_{weight} \times Y_{tbsa} \tag{1B}$$

An example of an equation to provide the modifiers for weight and total body surface area is $$Y = A + \frac{C}{(1 + Te^{-B(X-M)})^{1/T}} \tag{2}$$

Figure 4A:
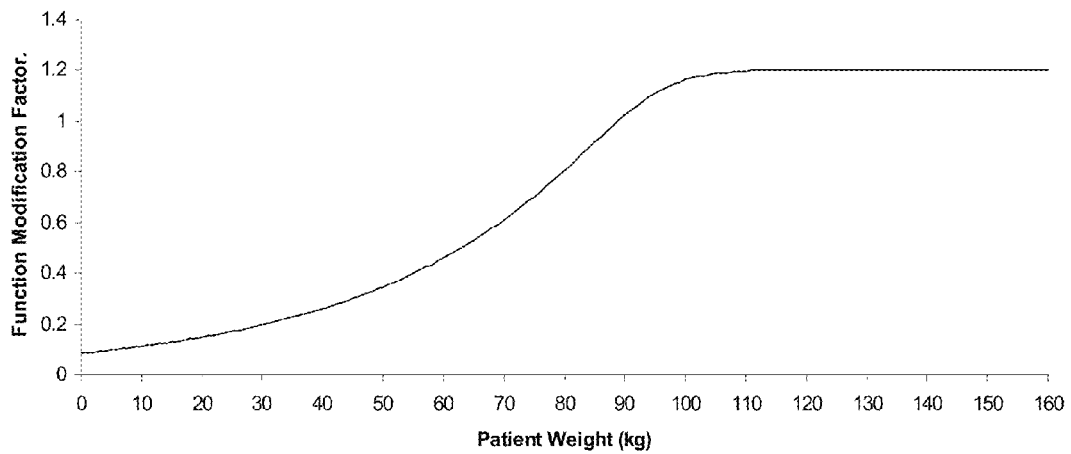
FIGS. 4A-4C depict different functions that are used in at least one embodiment to determine a new infusion rate.

FIG. 4A illustrates a graphical representation of a function that can be used for $Y_{weight}$ where the y-axis is the function modification factor and the x-axis is the patient's weight in kilograms. The modification factor is in the approximate range of 0.1 to 1.2 with it generally increasing with the weight of the patient before substantially leveling off around 100 kg. The illustrated function is produced by setting A equal to 0.001, C equal to 1.20, M equal to 93, B equal to 0.2, T equal to 7, and X equals the weight of the patient in kilograms.

Figure 4B:
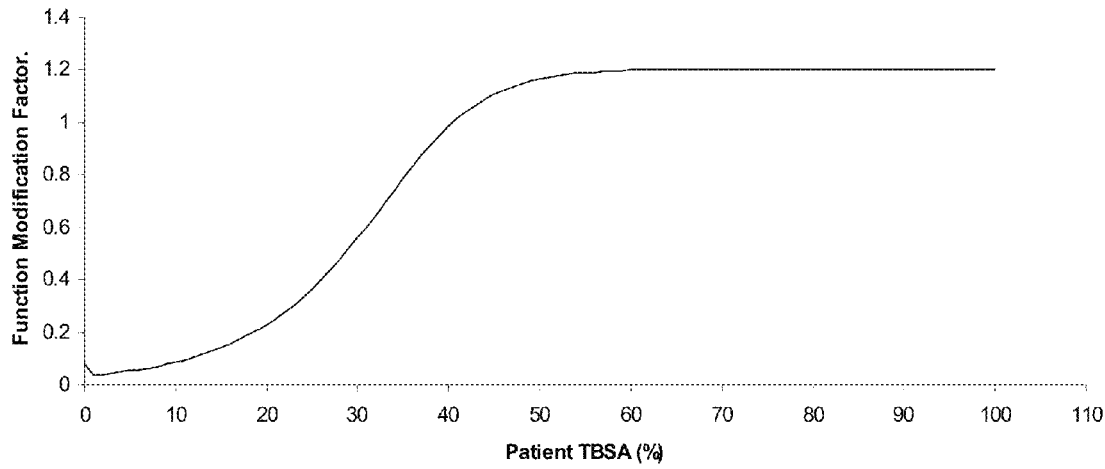
Figures 5A, 5B, 5C, 5D:
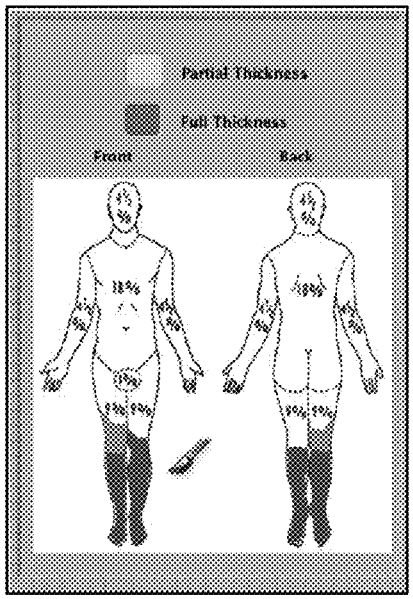
FIGS. 5A and 5B illustrate one example interface for entering information into the system.
FIG. 5C illustrates another example interface for entering information into the system.
FIG. 5D illustrates another example interface for entering information into the system.

FIG. 4B illustrates a graphical representation of a function that can be used for $Y_{tbsa}$ where the y-axis is the function modification factor and the x-axis is the patient's percentage total body surface area. The illustrated function is produced by setting A equal to 0.001, C equal to 1.20, M equal to 33, B equal to 0.2, T equal to 2, and X equals the percentage of total body surface area. The percentage of total body surface area could be manually entered by the user into a % TBSA data field in an interface and received by the system from, for example, the patient's electronic medical records. Or an interface similar to what is shown in FIGS. 5A and 5B could be used to assist the user in entering the estimated percentage of total body surface area into the system. FIG. 5A illustrates an interface that allows the user to paint 505 over a human representation 510 divided according to the Rule of Nines to show where the patient is burned and to what extent. Based on this information, the system calculates an estimate for % TBSA and outputs that estimate 515 as illustrated in FIG. 5B.

The interface illustrated in FIG. 5B provides an example of one way the patient's weight 520, time of injury 525, additional injury information 530 and other information might be entered into the system. The illustrated interface in FIG. 5B also illustrates an icon for obtaining an initial infusion rate 535. The percentage total body surface area can also be pulled from an electronic medical record for the patient or estimated using a Lund-Browder chart.

Figure 4C:
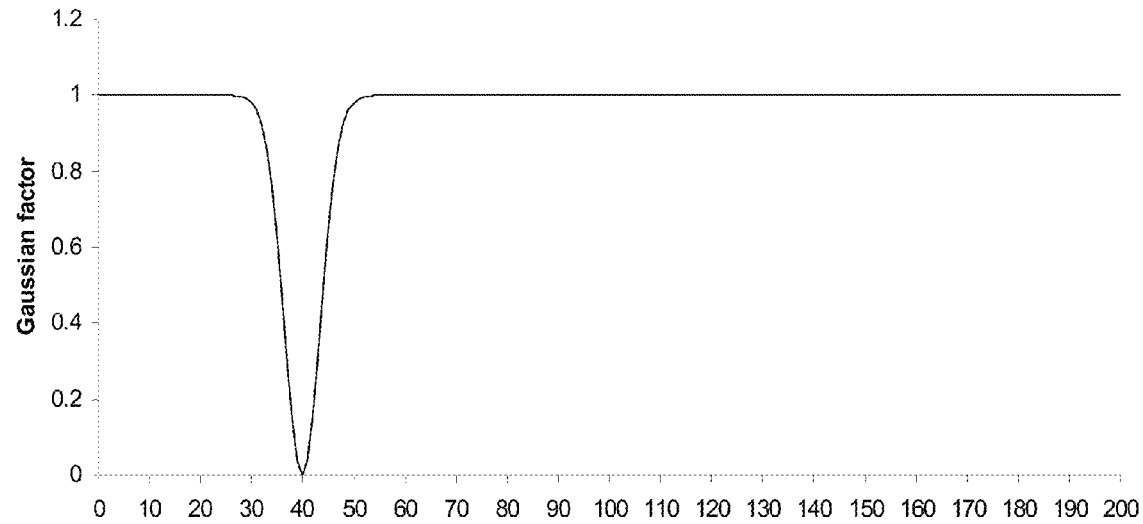

In a further embodiment, the new infusion rate equation is modified to include a Gaussian function. The addition of the Gaussian function reduces the change to the recommended infusion rate as the patient's urinary output approaches the target urinary output. FIG. 4C illustrates an example of a Gaussian function ($G_{UO}$) centered on a target urinary output of 40 mL/hr. An example of an equation that replicates the function illustrated in FIG. 4C is $$G = 1 - Ae^{-(X-B)^2/C^2} \tag{3}$$

where A is set to 1; X is set to the current urinary output; B is set to the target urinary output, which is 40 mL/hr in this example; and C is set to 5. There are at least two schools of thoughts regarding target urinary output. One school of thought is that the urinary output should be between 30 mL/hr to 50 mL/hr for a normal sized person. The second school of thought is that body weight impacts urinary output, so target ranges need to be normalized for the patient being cared for by the medical staff. For example, the value of B can be adjusted for a pediatric patient by selecting a value within the range appropriate for pediatric patients that is determined based on weight such that urinary output is normalized for weight. An alternative is to set the target urinary output (B) towards the end of the target range, which as discussed later in the burn field is 30 mL/hr to 50 mL/hr for adults, furthest from the current output and move the target urinary output towards the center as urinary output approaches the target range. The new infusion equation (1) becomes $$I_t = I_{t-1} + e(t) \times \frac{IRC_t}{UOC_t} \times Y_{weight} \times Y_{tbsa} \times G_{UO} \tag{1C}$$

Alternatively, any mix of the modifiers for the weight, the total body surface area, and the Gaussian function may be utilized. These modifiers are examples of infusion modifier values based on the described infusion model for burn patients that allow for the infusion rate to take into account additional information other than urinary output and as discussed below the level of modification is dependent upon where the particular characteristics fall in the respective functions.

Figure 6:
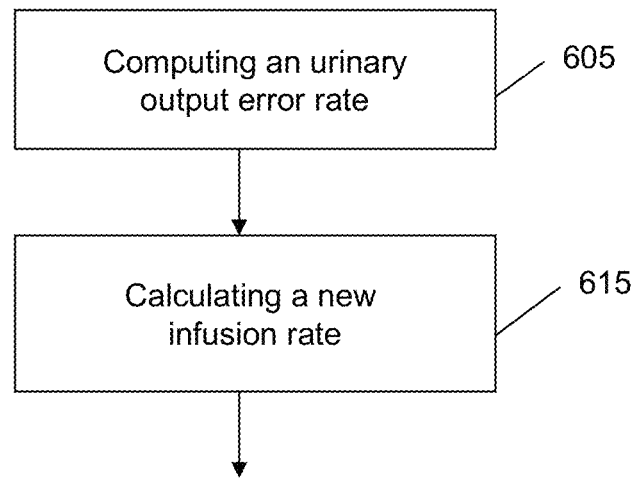
FIGS. 6-8 illustrate different embodiments for calculating an infusion rate.
Figure 7:
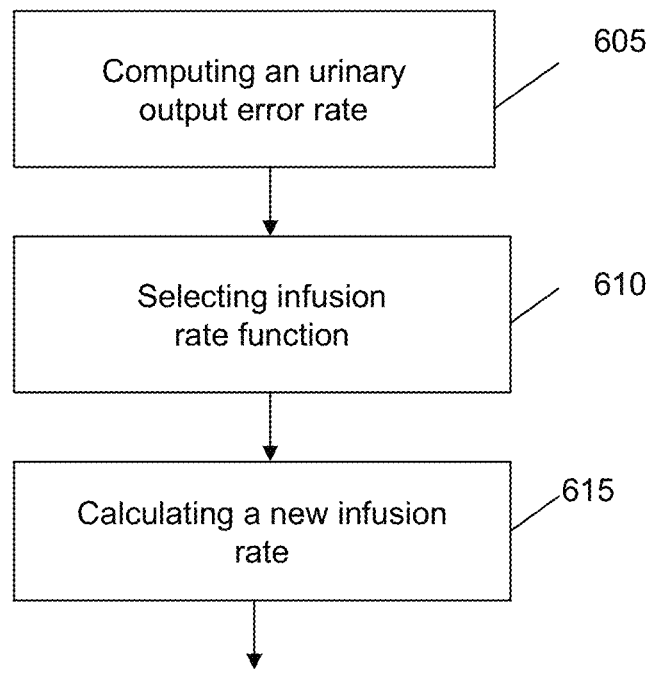

FIGS. 6 and 7 illustrate two different example embodiments for determining infusion rates that may be used in the later described methods for providing decision-support for resuscitation. Both examples make use of the urinary output, the last infusion rate, and the total body surface area in determining a new infusion rate.

FIG. 6 illustrates one example of how to calculate the new infusion rate ($I_t$) based on previously entered patient data including the total body surface area ($Y_{tbsa}$) and the patient's weight ($Y_{weight}$) and on information generated in the system including the urinary output, the last infusion rate, and the number of hours post burn. FIG. 5C illustrates an example of an interface that can be used to enter information regarding the patient and to identify different monitors (e.g., urinary output meter and infusion pump) that are providing information into the system. The illustrated fields allow for manual entry of the information either as textual information or a selection using graphical interfaces to setup the initial information regarding the patient in the system. Alternatively, as discussed above the infusion rate equation can take a variety of forms with the common basis for calculating including the last infusion rate, the current urinary output, and the hours post burn.

FIG. 6 illustrates the method based on the current urinary output, computing an error rate for the urinary output, 605. An example of an equation that can be used for this computation is $$e(t) = UO_t - UO_{target} \quad (4)$$

where $UO_t$ is the current urinary output that is obtained by the system and $UO_{target}$ is the target urinary output. The target urinary output in at least one embodiment for use with adults is selected from a range of 30 mL/hr to 50 mL/hr, and in at least one embodiment the target urinary output is set to 40 mL/hr. As discussed above, the urine target output can be normalized based on the patient's weight. An alternative is to set the target urinary output towards the end of the target range furthest from the current output and move the target urinary output towards the center as urinary output approaches the target range.

After the urinary output error (e(t)) is obtained, then a new infusion rate ($I_t$) is calculated, 615, using one of the above-described equations and their discussed alternatives. In this embodiment example, the infusion rate constant at time t is determined as follows:

$$IRC_t = 3.8975 e^{(5.828 - 0.035 HPB)} \quad (5)$$

where HPB is the hours post burn and e is the exponent function. A variety of equations that produce a decaying level for the infusion as the resuscitation progresses may be used for determining the infusion rate constant.

If a more frequent sampling of the urinary output occurs, then the above equations can be adjusted to reflect the increase in sampling, for example, the infusion rate constant ($IRC_t$) and the urinary output error (e(t)) with the example of 40 mL/hr would need to be proportionally adjusted from the current one hour sampling period. These example equations are set for sampling at 1 hour increments.

FIG. 7 illustrates an alternative method for calculating the new infusion rate that sets $IRC_t$ to a constant value for each of three phases. As occurs in FIG. 6, the urinary output error rate is obtained, 605. An infusion rate equation is selected based on the number of hours post burn, 710. The system can either run a timer to track the time since the burn occurred or use a comparison between the current time with time entered for the burn occurring. The selected infusion rate equation (or infusion rate function) is used to calculate the new infusion rate, 615.

Three phrases were selected based on empirical data obtained from regression studies of burn patient resuscitation. An example of the three phases is: Phase I—hours 0-13, Phase II—hours 14-33, and Phase III—34 hours and beyond. Typically during Phase I, the patient requires a massive infusion of fluid and will have instability in terms of cardiovascular function and variability in relationships between infused fluid and urinary output. Typically during Phase III, the patient will receive less fluid infusion and will become stable with the net fluid between infused fluid and urinary output decreases and/or becomes substantially stable. Using these three phase ranges, the $IRC_t$ constant is set as follows:

Phase I: −36.53 mL
Phase II: −21.55 mL
Phase III: −11.57 mL which represent the average rate of infusion change per each hour of each phase. The three $I_t$ functions based on equation (1) become Phase I
$$I_t = I_{t-1} + e(t) \times \frac{-36.53}{1.211} \quad (1D)$$

Phase II
$$I_t = I_{t-1} + e(t) \times \frac{-21.55}{1.211} \quad (1E)$$

Phase III
$$I_t = I_{t-1} + e(t) \times \frac{-11.57}{1.211} \quad (1F)$$

Figure 8:
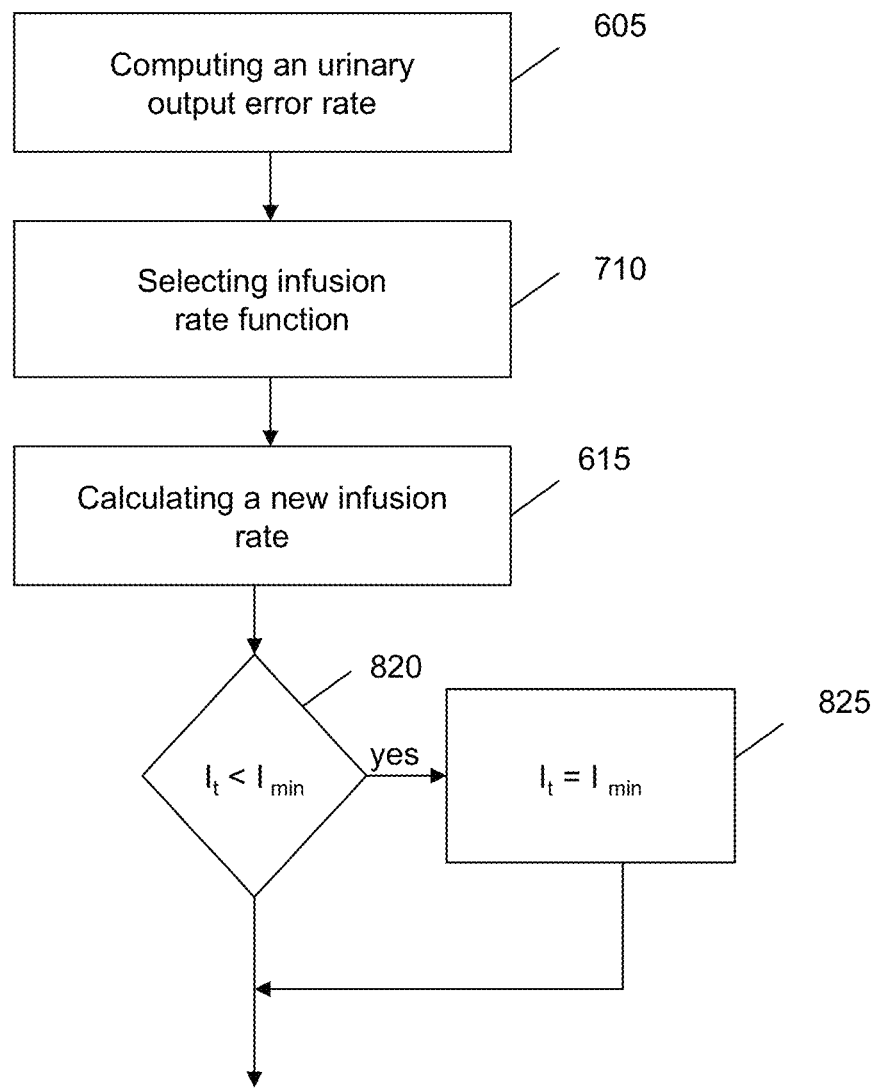

Either of the above methods illustrated in FIGS. 6 and 7 may further include setting an absolute minimum infusion rate ($I_{min}$) such as 125 mL/hr. FIG. 8 illustrates determining whether the new infusion rate ($I_t$) is less than a predetermined minimum infusion rate ($I_{min}$), 820. If the new infusion rate ($I_t$) is low, than setting the infusion rate ($I_t$) equal to a minimum infusion rate, 825.

Figure 9:
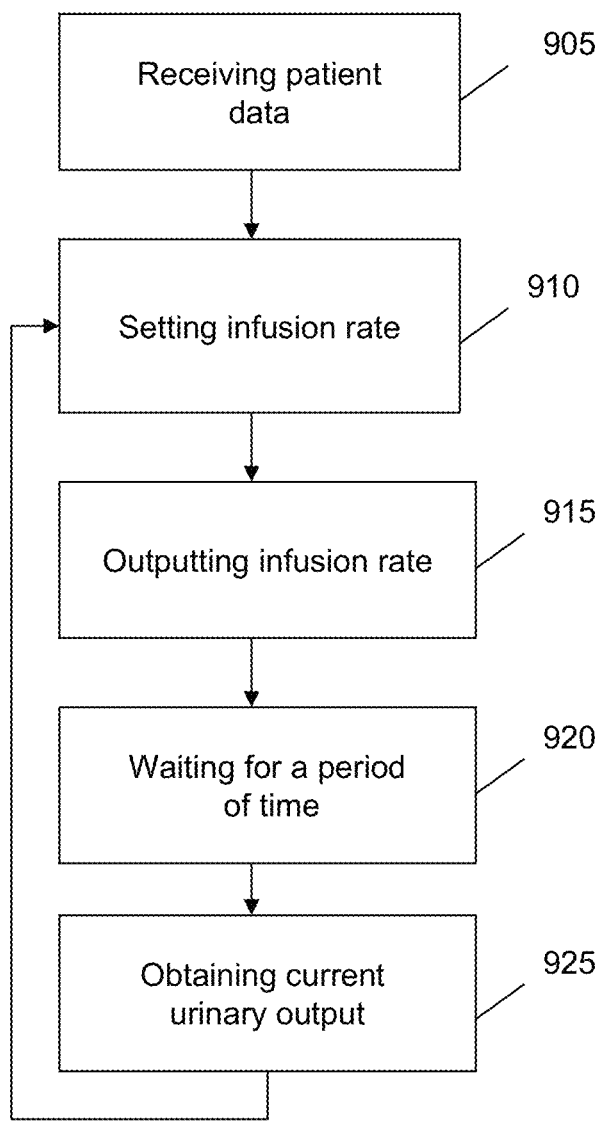
FIG. 9 illustrates an exemplary embodiment according to the invention.

FIG. 9 illustrates an embodiment for providing a recommendation regarding a new infusion rate. As illustrated, the method begins with the system receiving patient data, 905. The patient data received includes, for example, hours since the burn injury, the current urinary output, the current infusion rate, the patient's weight, and the patient's total body surface area. Additional examples of patient data include total urinary output prior to arrival 540 and total infusion prior to arrival 545 as illustrated, for example, in FIG. 5C. In some embodiments, at least a portion of this information is pulled from the patient's medical record. The minimum amount of patient data is dictated by the infusion rate calculation used by the method as described above and illustrated in FIGS. 6-8. The processor calculates an infusion rate, 910, based on the received data or current data when adjusting the infusion rate, 910. The infusion rate is determined using one of the methods described in connection with FIGS. 6-8.

Figure 10A:
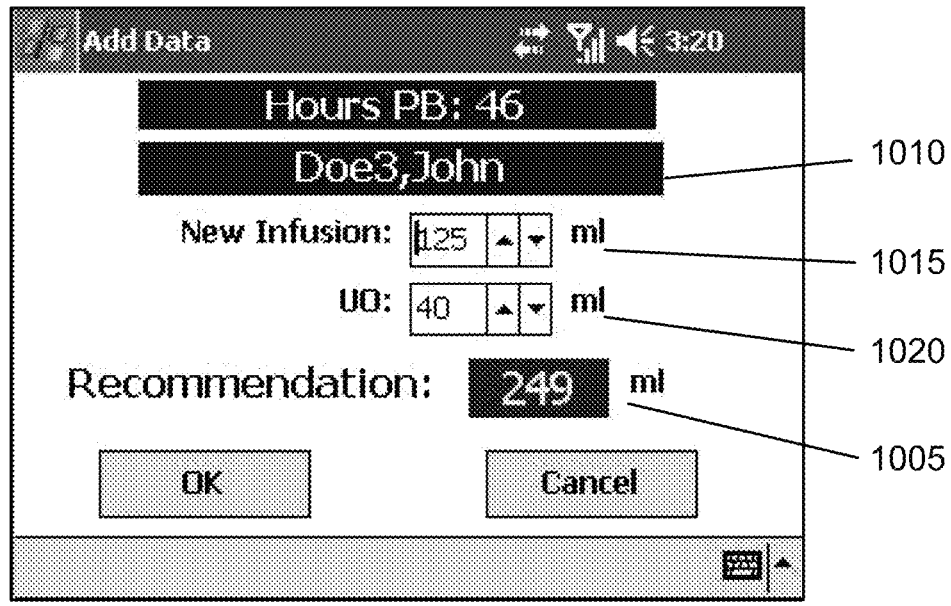
FIGS. 10A-10F illustrate different example displays for receiving and/or providing information to the user
Figure 10B:
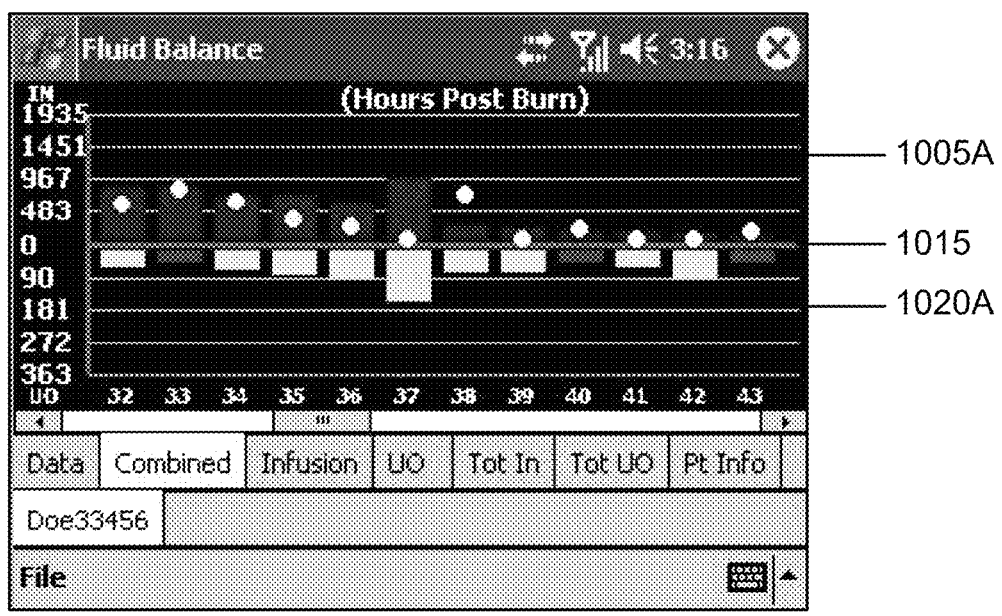
Figure 10C:
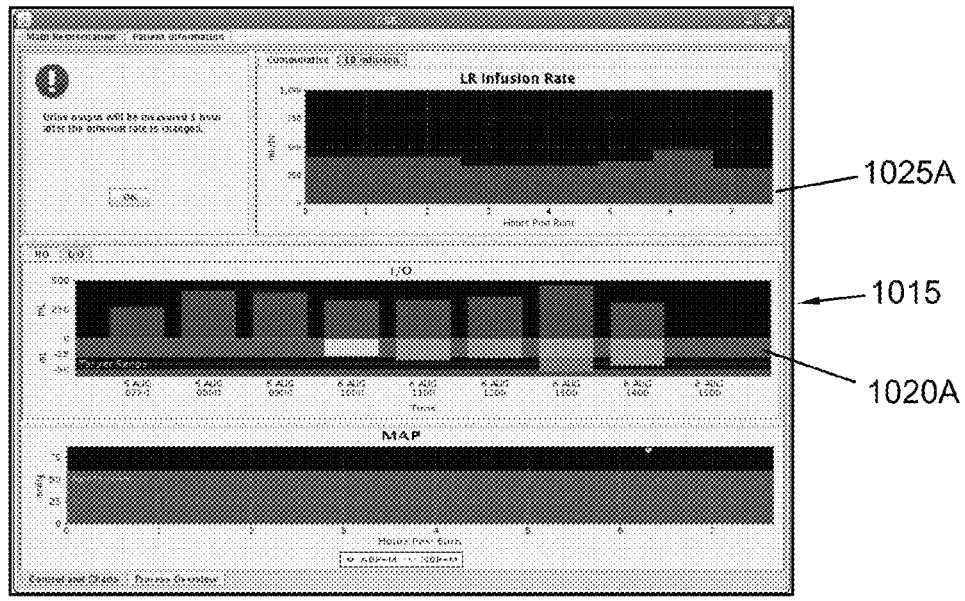
Figure 10D:
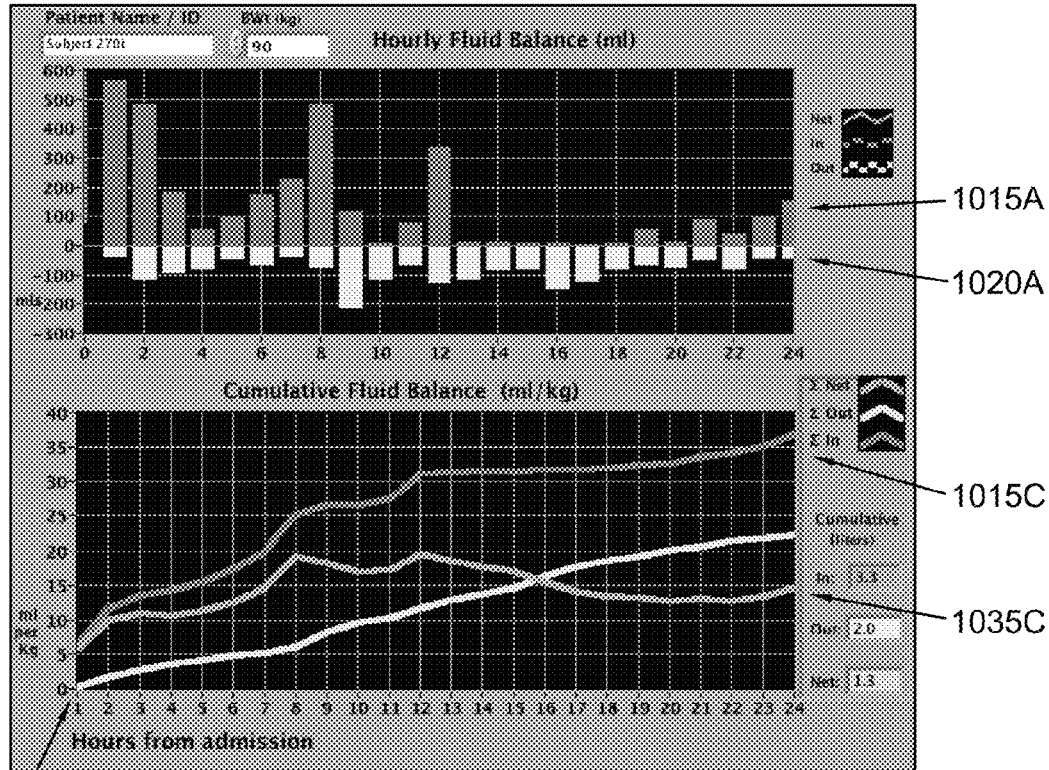
Figure 10E:
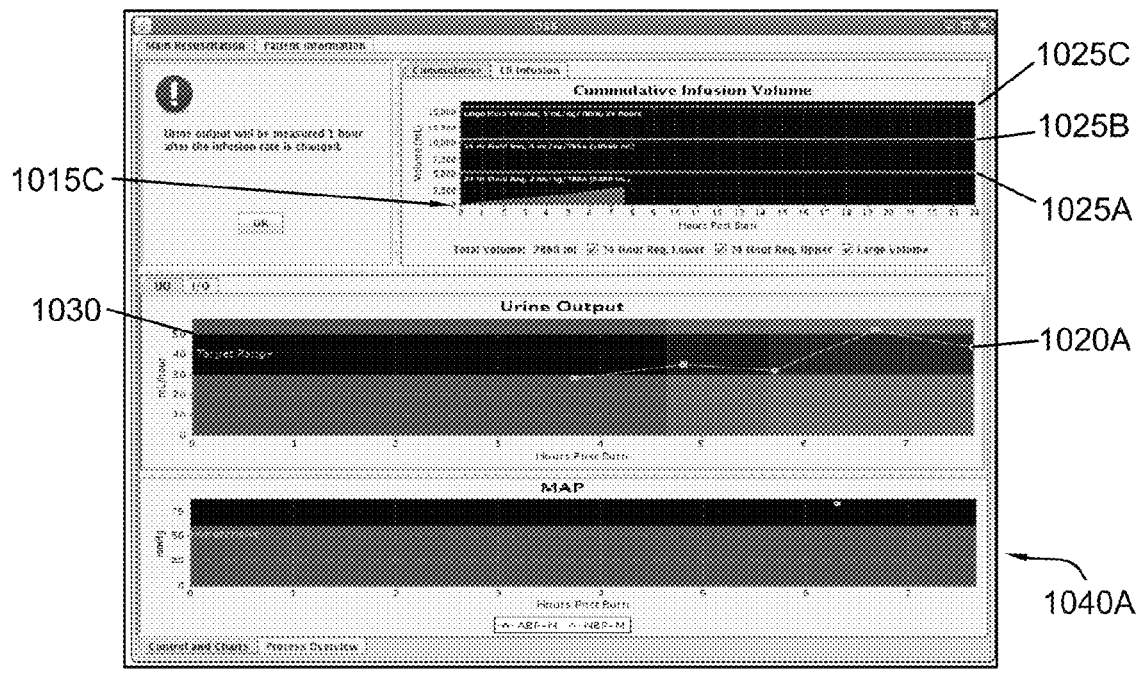

The processor outputs the infusion rate, 915. Examples of outputting the infusion rate include, for example, displaying the infusion rate, printing the infusion rate to paper, storing the infusion rate, sending a notification to medical staff, sending the infusion rate to a semi-closed-loop or closed-loop system to control operation of an infusion pump, sending a control signal to an infusion pump to adjust the infusion rate, and a combination of these. In a semi-closed loop system, outputting includes, for example, displaying the infusion rate for acceptance by the medical staff before sending a signal to an infusion pump of the value to a controller. Displaying the infusion rate includes, for example, providing the current recommended infusion rate as a number 1005 as illustrated in FIG. 10A and graphically versus time as illustrated in FIG. 10B-10D. FIG. 10A illustrates a display that shows the patient information 1010, the current infusion rate selected by the medical staff (e.g., the doctor) 1015, the urinary output 1020, and the recommendation for the new infusion rate 1005. FIG. 10A illustrates a situation where the medical staff has chosen to ignore the recommendation for the new infusion rate. In at least one embodiment, the system will require that a reason be provided for a change from the recommended infusion rate to document the care provided to the patient. FIGS. 10B-10D illustrate an interface that shows the infusion rate 1015A over the last few hours, also illustrated is a series of dots 1005A representing the recommend level of fluid infusion compared to the actual levels of fluid infusion provided to the patient. FIG. 10B was created based on a retrospective analysis of the full clinical record of a patient cared for at a top burn center and suggests that the invention will be more beneficial than current resuscitation approaches used in the medical field. FIGS. 10D and 10E illustrate an example interface that shows the cumulative infusion volume 1015C provided to the patient since the burn occurred. FIG. 10E also illustrates displaying infusion limits 1025A, 1025B, 1025C based on the patient's weight and percentage total body surface area (although in some embodiments, the percentage total body surface area is omitted) to provide guidelines to avoid abdomen pressure buildup and thus reduce the risk of morbidity.

The processor in at least one embodiment waits for a period of time before calculating a new infusion rate, 920. A period of time is allowed to elapse such as 5 minutes, 10 minutes, 15 minutes, 30 minutes, or 60 minutes although over periods of time could be used in a range of 1 minute to 90 minutes depending upon, for example, whether the output is being provided to medical staff in a semi-closed loop system or a closed-loop system. In a closed-loop system, the wait time is preferably under 20 minutes to allow for quicker response and adjustment of the infusion rate to reflect changes in the patient. In contrast, the semi-closed loop system will have wait times that are longer to lessen the impact upon the medical staff needing to interact with the system. In at least one embodiment for the semi-closed loop system, the user sets the wait time to reflect the staffing situation and other factors beyond the control of the semi-closed loop system. Alternatively, the wait delay for the first time through the method may be shorter to provide an initial urinary output and to allow for the infusion rate to be adjusted sooner to reflect the patient's condition. When the method is repeated again, the length of the delay is determined based on the current condition of the patient. Less frequent checks are desirable to lessen the impact on the medical staff in terms of monitoring the patient, although the frequency should be at least once per hour. In at least one embodiment, the wait time is adjusted based on whether certain urinary outputs conditions have been met. For example, if any of the urinary output determinations are positive, then the method can set the wait time to a shorten time period.

After waiting for a period of time, the processor obtains the current urinary output, 925. Different ways to obtain the urinary output include, for example, a device measuring the urine volume, a drop rate sensor measuring the amount of fluid passing from the urine catheter, or a manual entry of volume from a visual inspection by the medical staff. The urinary output can be based on a variety of approaches that prorate/extrapolate the flow to the appropriate length of time such as one hour. The urinary output can be based on, for example, a running one minute average for the last five minutes extrapolated to an hour flow rate, the extrapolated flow based on the last five or ten minutes to an hour flow rate, and the captured flow for the last sampling period adjusted to an hour flow rate. This will allow a modification of the hourly model and allow the decision assist method to be used as part of a closed-loop system that adjusts the infusion rate, for example, every five minutes. In an embodiment that is implemented, the processor receives a urinary output as a volume amount that is converted into a flow rate based on the difference in volume since the last urinary output reading divided by the time difference, which in some embodiments is normalized to a one hour period or other wait delay period.

Figure 10F:
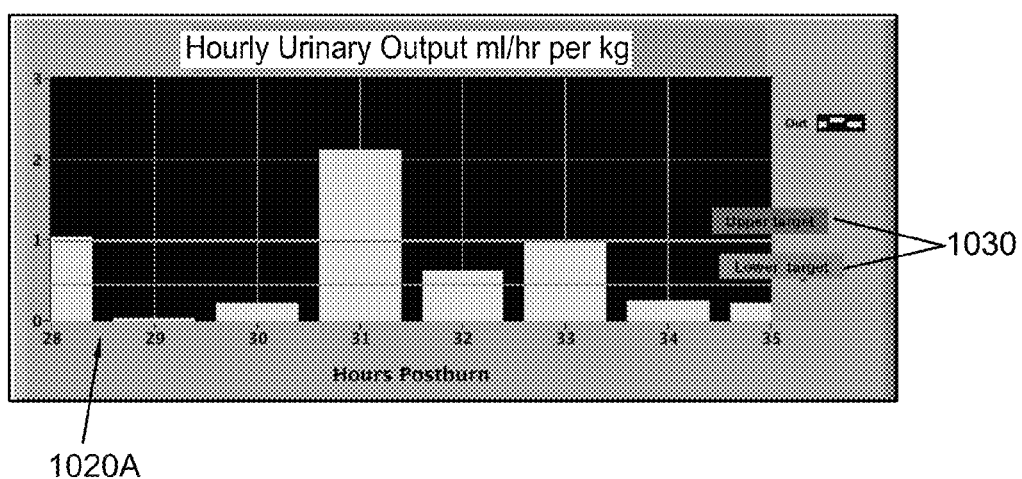

An alternative method includes displaying information regarding the urinary output of the patient in addition to infusion rate information as illustrated, for example, in FIGS. 10A-10E. FIG. 10A illustrates the urinary output as a number 1020 in mL/hr. FIGS. 10B-10E illustrate the information being provided over time 1020A to assist the medical staff in treating the patient and potentially noticing trends that may be occurring. FIGS. 10C, 10E, and 10F illustrate the inclusion of a target range for urinary output 1030. FIG. 10D illustrates the cumulative total for urinary output 1020C and a cumulative net fluid retention 1035C. Alternatively, the net fluid balance may be presented to the medical staff so that trends can be acted upon if needed. The timing and extent of the response (if any) exhibited by the patient provides confirmation as to whether the current fluid therapy approach is working and whether the medical staff may need to try a different treatment approach.

In at least one embodiment, the user interface for the system includes, for example, a graphical element, button, or other similar mechanism for the medical staff to mark when a physiologic "challenge" is given to the patient. A benefit to displaying the infusion rate versus time 1015A along with the urinary output versus time 1020A is that when a bolus or some other physiologic "challenge" is delivered to the patient to test the patient's volume responsiveness, then that information can be determined by visual inspection of the graphical presentation. In at least one other embodiment, the magnitude of the urinary output response and the delay between the challenge and the urinary output response is determined by the system based on the time course of the urinary output. The method takes this information into account to assess if the patient's urinary output is responding to the infused volume. When a patient does not respond well, a larger bolus or higher infusion rate can be recommended as part of the method. However, there is an upper limit of infusion rate that can be safely utilized. Thus, when a patient is a non-responder the medical staff is alerted for consideration of other techniques, such as cardiovascular drugs.

An alternative embodiment for setting an initial infusion rate is to use either the Brooke or Parkland formulas. Another alternative embodiment is to use a predetermined infusion rate as the initial infusion rate to attempt to expedite obtaining urinary output in the target range. A further alternative embodiment uses the Rule of Tens to set the initial infusion rate. For example, for a patient who ways 80 kg or less the percentage of total body surface area is multiplied by 10 to set the infusion rate in mL/hr; and when the patient's weight exceeds 80 kg, for every 10 kg in excess of 80 kg of the patient's weight, an additional 100 mL/hr is added. In yet another alternative embodiment, if there is urinary output, then the initial infusion rate is calculated using an equation based on the patient model.

Figure 11A:
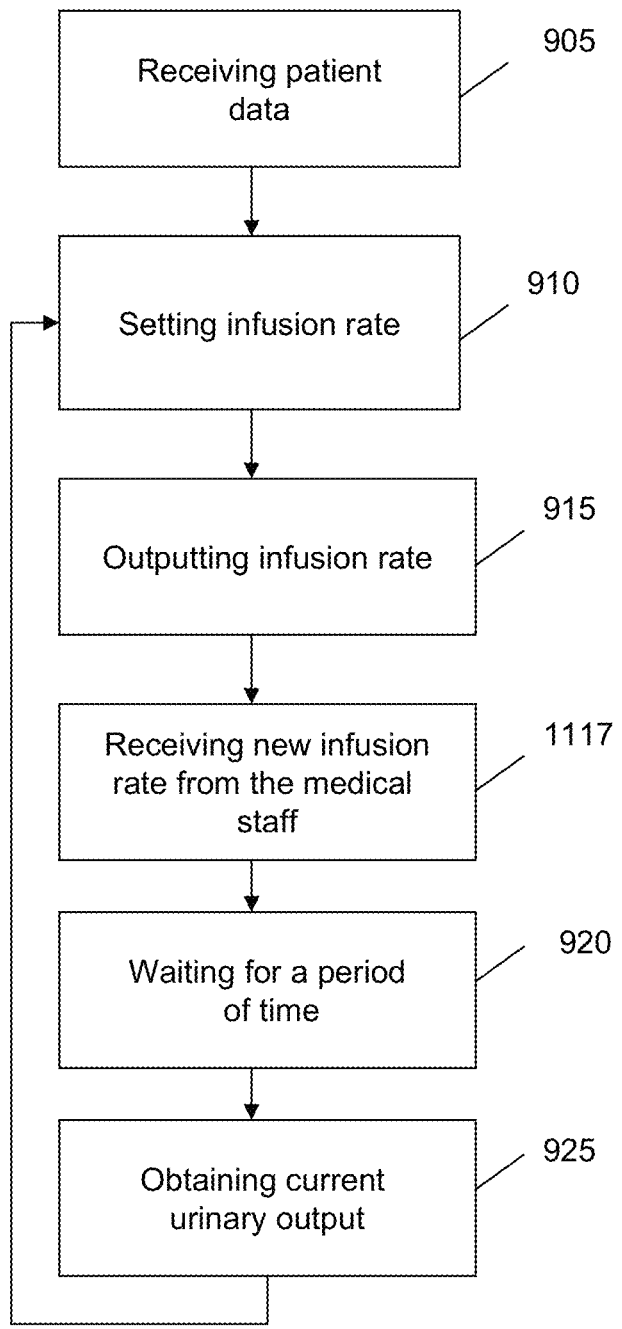
FIGS. 11A and 11B illustrate different alternative embodiments according to the invention.

FIG. 11A illustrates a modification to the method illustrated in FIG. 9 that includes receiving the new infusion rate from the medical staff, 1117. As discussed above in connection with FIG. 10A, the medical staff can chose to ignore the recommendation of the decision-assist system in a semi-closed loop implementation or when the system is operating as a decision-assist system. When this occurs, the received infusion rate is used for calculating the new infusion rate the next time it is calculated instead of using the previous recommended infusion rate.

Figure 11B:
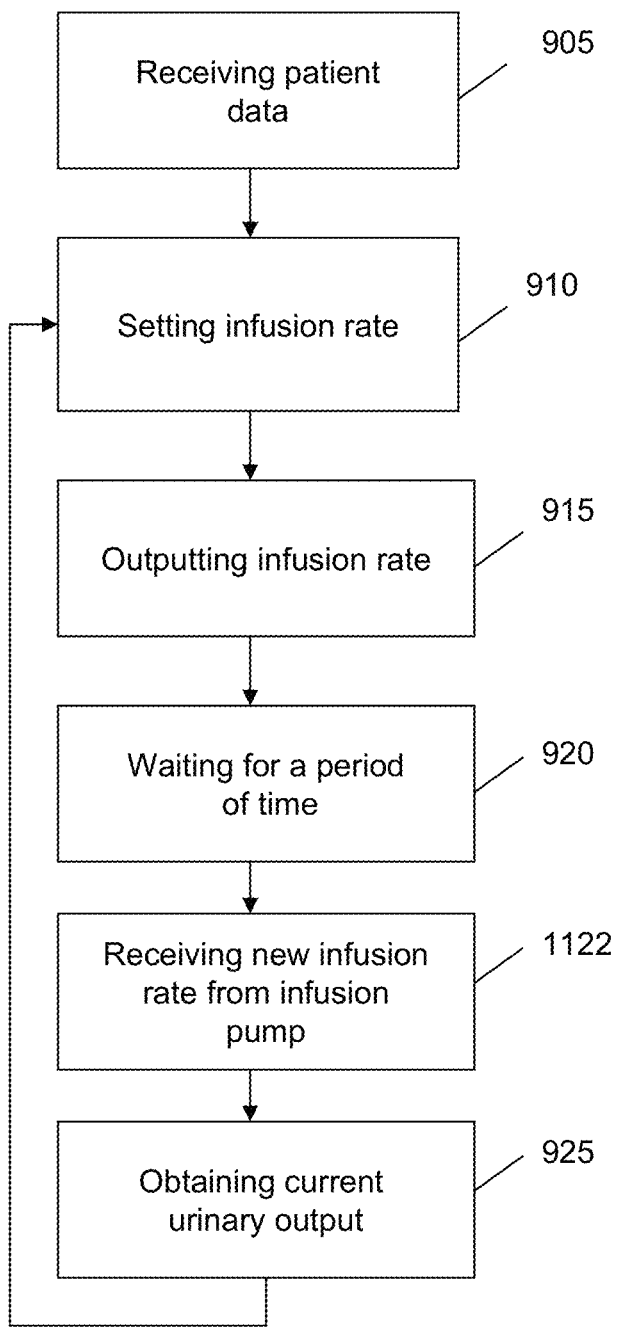

Alternatively, the system can receive from the infusion pump the actual infusion rate provided to the patient, 1122 as illustrated in FIG. 11B. The receiving of the actual infusion rate although illustrated as occurring prior to obtaining the current urinary output, receiving of the actual infusion rate can occur at any point between calculations of an infusion rate.

Figure 12A:
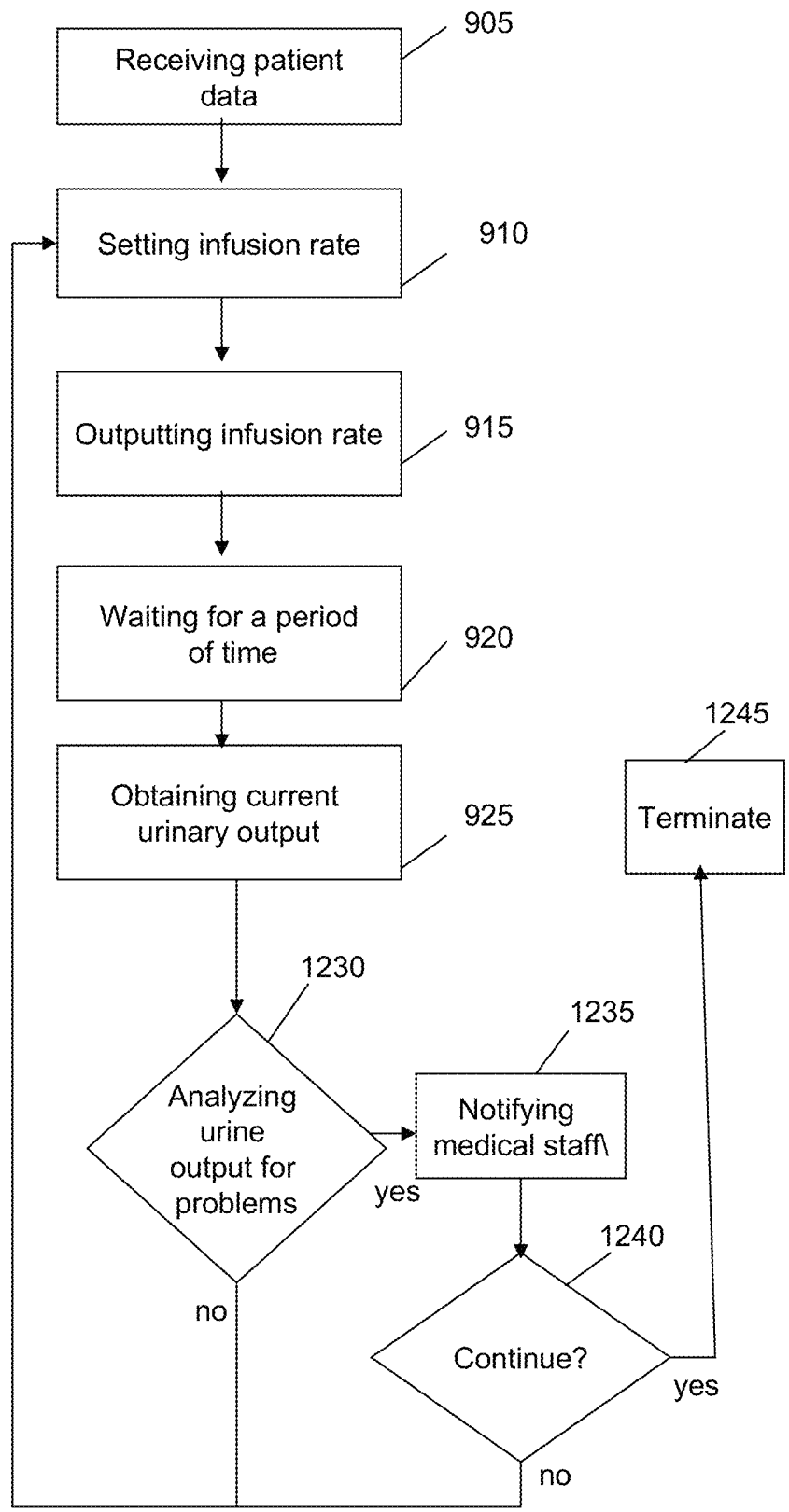
FIGS. 12A-12C illustrate different alternative embodiments according to the invention relating to problem detection.

FIG. 12A illustrates a modification to the method illustrated in FIG. 9 and its alternatives. The process covered by 1230 and 1235 can occur as illustrated after obtaining current urinary output 925, but this process can occur before obtaining current urinary output 925 or before waiting for a period of time 920. Analyzing the urinary output for problems, 1030, such as erroneous or out of range urinary outputs. Examples of problems to analyze include low urinary output resulting from equipment failure, renal failure, inadequate perfusion of the kidneys typically due to low cardiac output or low renal perfusion, or the patient is otherwise non-responsive to the resuscitation. If a problem is determined to exist, notifying medical staff of the problem, 1035. Examples of the notification include, for example, sounding a visual or audio alarm in the monitoring system connected to the patient including bedside monitors and/or remote nurse's station monitoring equipment; sending an alarm notice to communication devices such as a pager, cellular telephone, or a telephone; sending an e-mail or text message to designated recipients; and any combinations of these. The notification in at least one embodiment includes a recommendation(s) as to how to proceed such as to check the equipment or consider inotropes. The type of notification can be reflective of the problem or potential problem detected. If the urinary output does not satisfy a problem condition(s), then calculate a new infusion rate, 920.

FIG. 12A also illustrates alternative processes to problem detection. Receiving an instruction in response to the notice sent in 1235 to medical staff, 1240. Ending the process if the instruction is to terminate, 1245. Returning to the main process flow if the instruction is to proceed. In an alternative embodiment, the method includes setting a time limit to receiving the instruction in 1240 before proceeding with the method if no instruction is received.

An alternative embodiment allows for the medical staff to terminate the process if the patient stabilizes during the resuscitation or a problem has been detected independent of the method. When the patient has stabilized, this is an indication that the resuscitation has been completed. An example of this is shown in FIG. 10D at the right arrow, where the net fluid level is shown as declining for a period of time, which is an indication that the inflammatory process after the burn is ending as capillary leakage has been substantially repaired and the patient is having adequate fluid retention at this point. One recognized definition for the patient becoming stable is that urinary output is adequate with near maintenance level of fluid for three or more hours, and in some embodiments the time threshold is six hours when the resuscitation is between 24 and 48 hours. Another recognized definition requires that the patient has reached hemodynamic stability prior to resuscitation being ended. The system upon receiving such a notification would terminate and treat the notification like an interrupt. In at least one embodiment, the system monitors the urinary output and the infusion rate to determine whether the criteria for stability have been satisfied for a period of time. In another embodiment, the system receives additional inputs regarding blood flow, blood pressure, and heart rate to allow for a determination to be made as to whether hemodynamic stability has been obtained. An example of this is the mean arterial pressure 1040A being tracked by the system.

Figure 12B:
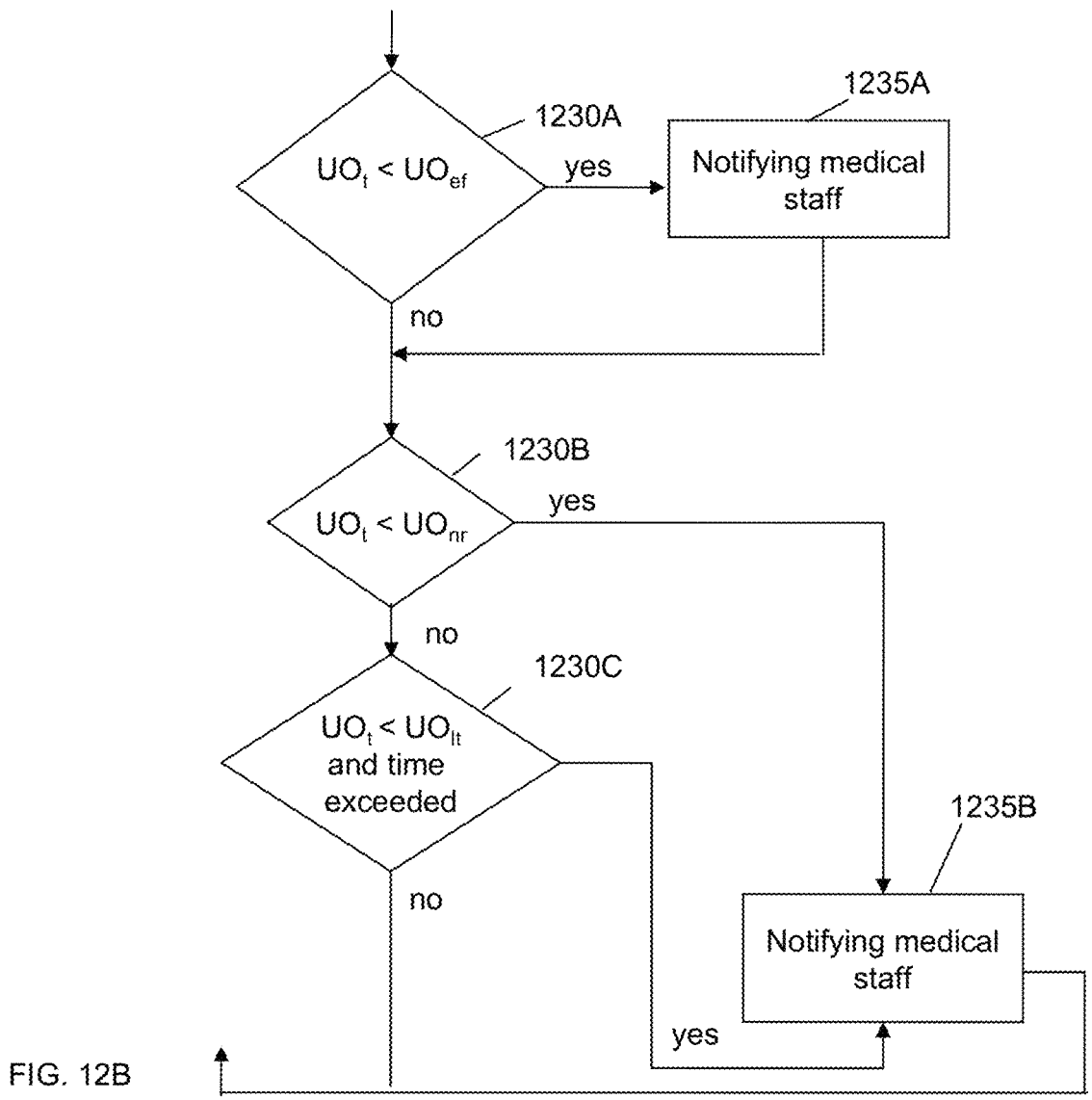

FIG. 12B illustrates an example of analyzing a couple of different urinary output problems. Alternatively, different combinations then those illustrated could be used and these steps may be reordered. As illustrated, the current urinary output ($UO_t$) is analyzed to determine whether it is below an equipment failure threshold ($UO_{ef}$), 1230A. The equipment failure threshold preferably is set at 5 mL/hr or its equivalent rate. However, the equipment failure threshold could be selected from a range of 0.5 mL/hr to 15 mL/hr. The equipment failure threshold is set to allow for detection when there may be a problem with the bladder catheter, for example, being blocked, kinked, removed, or disconnected resulting in no or little urinary output. If this condition is satisfied, then notifying the medical staff, 1235A, of the potential problem.

If the urinary output ($UO_t$) exceeds the equipment failure threshold ($UO_{ef}$), then determining whether the current output satisfies non-responsiveness criteria, 1230B, 1230C. If the non-responsiveness criteria are satisfied, then notifying the medical staff, 1235B. Examples of non-responsiveness criteria include low current urinary output and low urinary output for a predetermined amount of time.

Determining whether the urinary output ($UO_t$) is below a non-response threshold ($UO_{nr}$), 1230B, and when it is, then notifying the medical staff that the patient may be non-responsive and an intervention may be required, 1235B. The non-response threshold ($UO_{nr}$) is illustrated in FIG. 12B, and may be, for example, 15 mL/hr. Alternatively, this determination can also require that the current infusion rate be above a current infusion threshold that in at least one embodiment is dictated by the hours post burn. An example is in Phase I the threshold is 500 mL/hr, Phase II the threshold is 300 mL/hr, and Phase III the threshold is 150 mL/hr.

If the urinary output ($UO_t$) is in excess of the non-response threshold ($UO_{nr}$), then determining whether the urinary output ($UO_t$) is below a target range ($UO_{tt}$) for a low time threshold, 1230C. Alternatively, this determination can also require that the current infusion rate be above a current infusion threshold as discussed, for example, in the paragraph above. If this determination is positive, then notifying the medical staff that the patient may be non-responsive and an intervention may be required, 1235B.

Figure 12C:
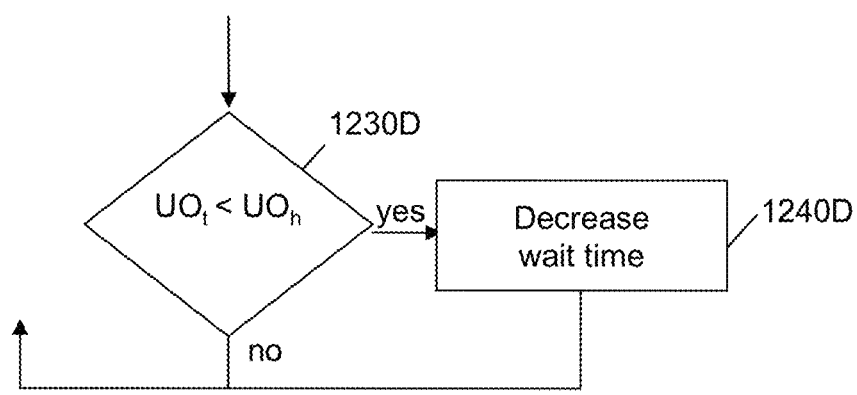

As illustrated in FIG. 12C, the method in one embodiment includes a urinary output determination based on the urinary output ($UO_t$) exceeding a target range ($UO_h$), 1230D. As discussed above in different examples, the high end of the target range ($UO_h$) may be 50 mL/hr, but that this range can be adjusted based on current medical approaches. If the determination is positive, then setting the wait time to a reduced period of time, 1240D instead of providing a notification, 1235. Then determining a new infusion rate, 910. In another embodiment the criteria to be satisfied in this determination includes that a high time threshold is also satisfied, and in such a situation a notification is provided to the medical staff, 1230.

An alternative embodiment when the problem embodiments are used is to include a check to see if the urinary output is within the target range, and if it is then to proceed to the calculation of the infusion rate, 615.

Additional examples of problems or other triggers that can serve as a basis for alerting the medical staff in some embodiments include different infusion rates being used for the first time or for a period of time, size of the infusion rate change, cumulative infusion rates exceed certain thresholds, projections exceed certain levels, and mean arterial pressure and other physiological conditions unrelated to urinary output. Examples of infusion rates used for the first time include 125 mL/hr, 1000 mL/hr, and 2000 mL/hr. Examples of a change in the infusion rate include greater than 30% of the previous infusion rate or 500 mL/hr. from the previous infusion rate. Another example of a trigger is if the average infusion rate exceeds 1000 mL/hr for six hours. Examples of cumulative infusion rates exceeding certain thresholds include total volume greater than 200 mL/kg in 24 hours or less (in at least one embodiment accompanied by an early warning) and 250 mL/kg in 24 hours or less (in at least one embodiment accompanied by a severed warning). An example of a projection is if the 12 hour cumulate volume will exceed 250 mL/kg. Examples of physiological conditions include urinary output less than 10 mL; mean arterial pressure less than 60 when urinary output is greater than 50 mL, and in such a situation in at least one embodiment the recommended infusion rate will maintain the previous infusion rate in an attempt to increase the mean arterial pressure; and sodium at hour 24 is less than 150, recommend continuation of LR and otherwise recommend to modify fluid being used. Other lab values or chemistry could be used such as whether the patient is acidotic (i.e., base deficient). Another potential trigger is that if the abdominal compartment pressure (measured for example with sensor placed in the bladder via Foley catheter) has increased rapidly or exceeded a predetermined threshold, then alerting the medical staff that the fluid therapy may need to be changed to avoid injuries associated with over-resuscitation and to avoid the need to make an incision into the abdomen.

Figure 14:
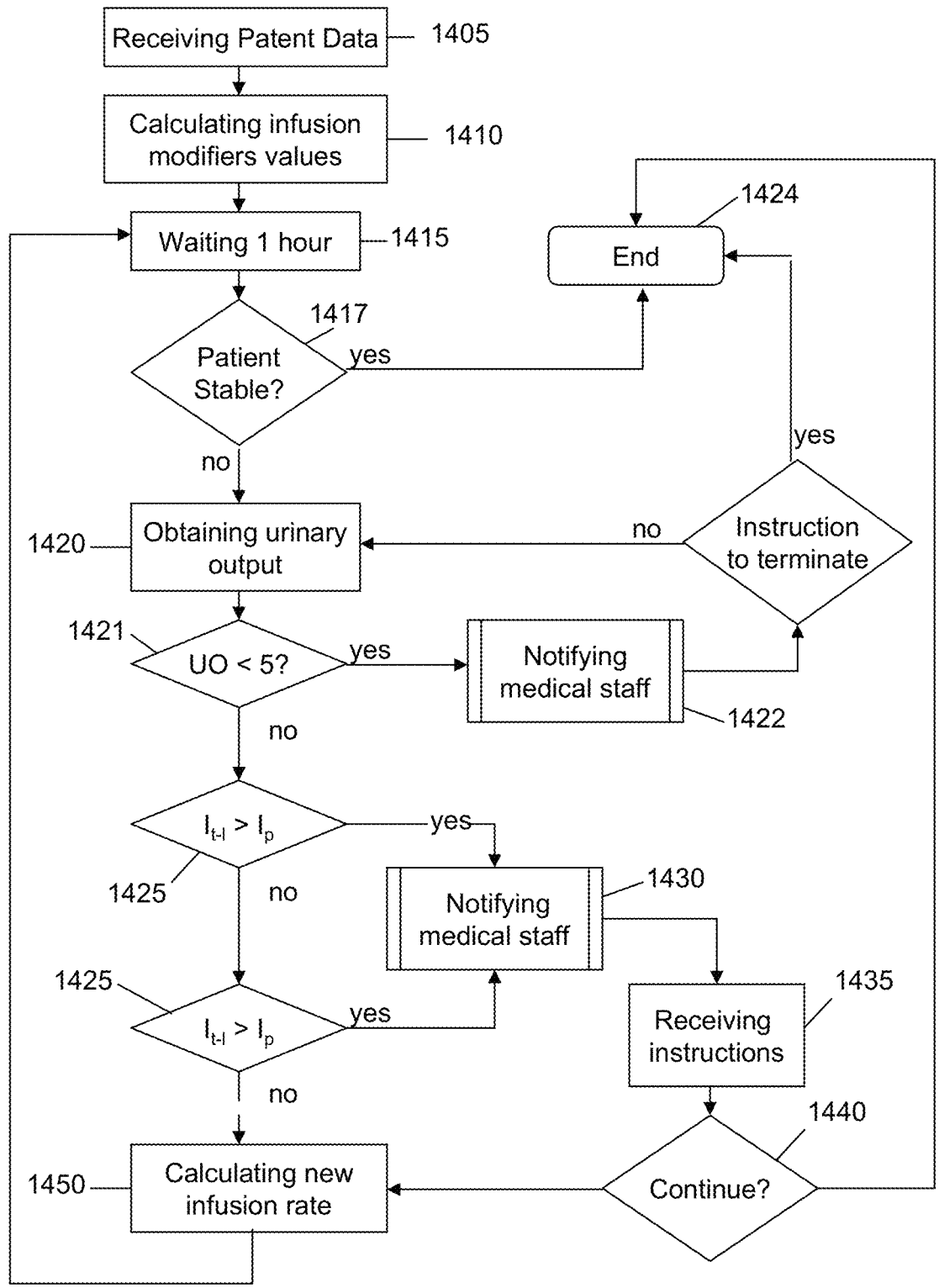
FIG. 14 illustrates an embodiment using different aspects of the preceding embodiments as an example according to the invention.

In at least one embodiment after or before the wait period, the method includes a determination as to whether the patient has stabilized (although this determination could occur at any point in the method and act as an interrupt). FIG. 14 provides an example of this determination. The determination includes in at least one implementation receiving a notification from the medical staff that the patient has stabilized. In another implementation, the determination is made by the system based on physiological readings for the patient. Both of these implementations can be combined. Upon receiving a notice or determining the patient has stabilized, terminating the resuscitation.

In at least one embodiment, the method further includes a variety of limit checks when calculating the new infusion rate. Examples of limit checks include infusion rate between 125 mL/hr and 2000 mL/hr, maximum change of 500 mL/hr or a predetermined percentage such as ±20%, and no decrease in infusion rate when mean arterial pressure is less than 60 and urinary output is greater then the target range. In other embodiments, the method recommends termination of the resuscitation when 48 hours has elapsed in an ICU setting or 72 hours has elapsed in an PDA setting, and the infusion rate has been at maintenance level (e.g., 125 mL/hr or less) for a period of time (e.g., six hours between hours 24 and 48). In at least one embodiment the system will run for at least the first 24 hours post burn before terminating.

Certain conditions have been shown to not necessarily work with the above-described resuscitation method. The contraindications include abnormal renal function, administration of diuretics (urinary output will be greater than normal), elevated blood alcohol level, severe electrical injury, rhabdomyolysis requiring urinary output between 30 and 50 mL/hr, acute MI, and cutaneous burns less than 20% TBSA. Even when these conditions exist, the medical staff may still utilize the invention in a resuscitation.

Figure 13:
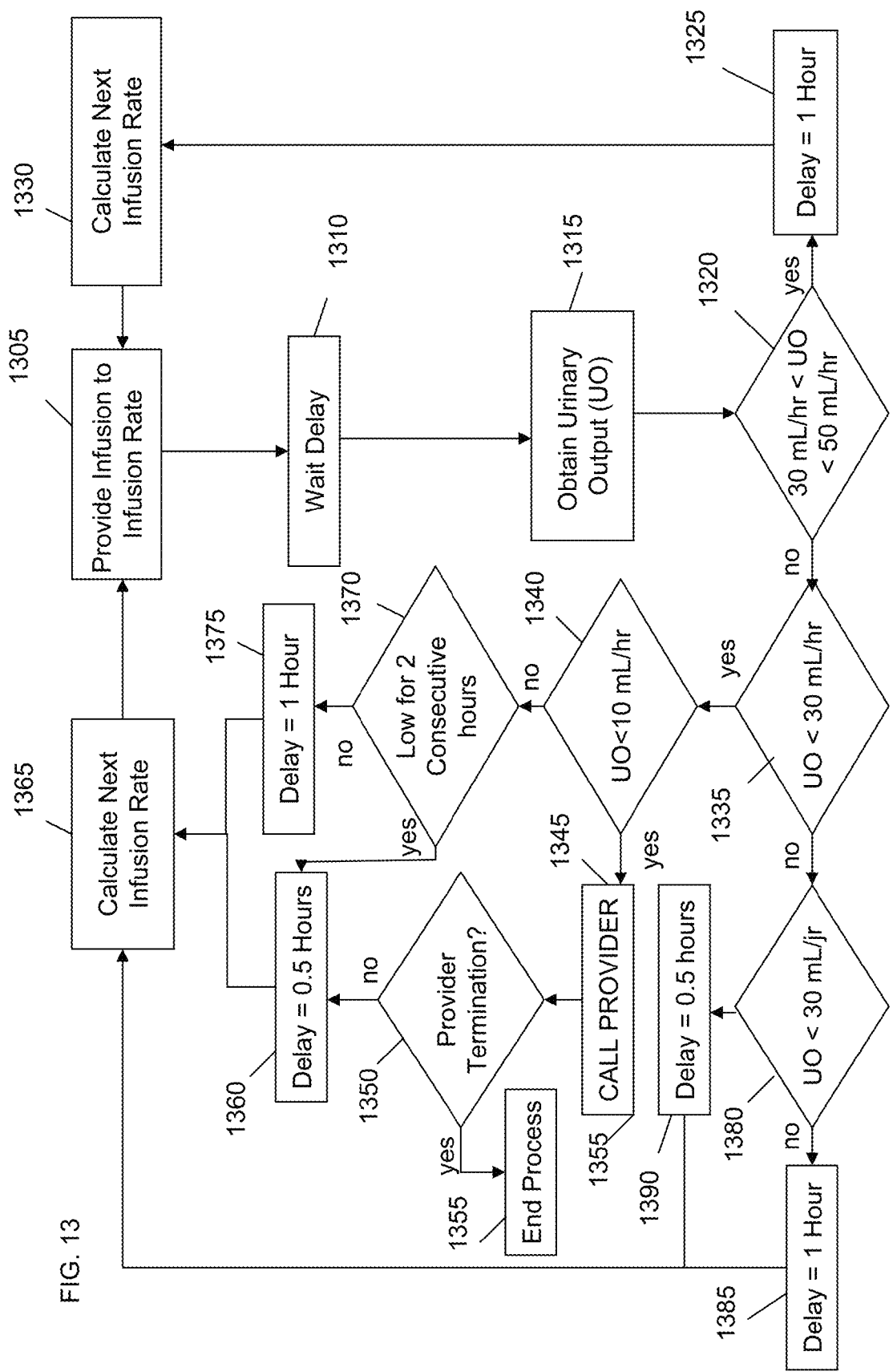
FIG. 13 illustrates an embodiment using different aspects of the preceding embodiments as an example according to the invention.

FIG. 13 illustrates an implementation example of the method using different aspects discussed above in connection with different embodiments. Once the patient has been prepared to start the resuscitation including connection of an infusion line and a catheter to the patient. The initial infusion rate is set for an infusion pump to deliver fluid to the patient, 1305. A period of time is allowed to elapse such as 10 minutes, 15 minutes, 30 minutes, or 60 minutes although over periods of time could be used in a range of 5 to 90 minutes, 1310. Examples of how to maintain the wait delay include, for example, a timer with or without an alarm that is displayed or not displayed for viewing by the medical staff. Alternatively, the wait delay for the first time through the method may be shorter to provide an initial urinary output and to allow for the infusion rate to be adjusted sooner to reflect the patient's condition. In at least one embodiment when the method is repeated again, the length of the delay is determined based on the current condition of the patient. Less frequent checks are desirable to lessen the impact on the medical staff in terms of monitoring the patient, although the frequency should be at least once an hour. However, if the output is sent to a closed-loop system, then the frequency will increase. The urinary output is obtained for the period of the wait delay to determine the flow rate in milliliters per hour, 1315.

The urinary output is compared to a predetermined range to see if it falls within the range, 1320. The illustrated range is 30 mL/hr to 50 mL/hr, which represents the current target range for urinary output for adults during resuscitation. One of ordinary skill in the art will appreciate based on this disclosure that this range may be adjusted based on current thinking regarding the optimal urinary output or to be adapted for pediatric care. If the urinary output is in the desired range, then the wait delay is set for 1 hour, 1325. Although this wait period can be a variety of lengths as discussed above but given that the urinary output is in an acceptable range the wait delay can be longer to minimize the impact on staff resources. The infusion rate is calculated, 1330, prior to setting the infusion rate, 1305.

However, if the urinary output is outside the range, then a determination is made as to whether the urinary output is below the target range, 1335. Alternatively, the determination could be based on whether the urinary output is above the target range and reversing the yes/no for the two branches leading to 1340 and 1380. This is an indication that the infusion rate needs to be adjusted potentially upwards to elevate the urinary output for the patient.

If the urinary output is low, then it is determined if the urinary output is below a predetermined problem threshold, 1340. The predetermined problem threshold allows for the medical staff to be notified if the urinary output is such that there may have been a system failure or the patient has become non-responsive. The illustrated predetermined problem threshold in FIG. 13 is 10 mL/hr, or as discussed above in connection with FIG. 12B, this threshold could be 5 mL/hr. If the urinary output is below the predetermined problem threshold, then the medical staff is alerted to a potential problem, 1345, to allow for the medical staff to confirm that the system is working, for example, that the catheter has not been compromised, or that the patient is becoming non-responsive and a new course of medical treatment may be required. A termination decision is received from the medical staff on whether the process should continue, 1350. If the termination decision is yes, then the process is ended, 1355. If the termination decision is no, then the wait delay is set to a shorter period of time that is less than the regular wait delay to increase the frequency of the checks to speed up the process of bringing the urinary output in the target range, for example, the illustrated wait delay is set to 30 minutes, 1360. A new infusion rate is determined, 1365. FIGS. 5-8 provide examples of how the new infusion rate may be determined.

If the urinary output is in excess of the predetermined threshold in 1340, then it is determined how long the urinary output has been below the target range, 1370. The illustrated low output time threshold is two hours in 1370. There are a variety of ways that the length of time can be determined including finding the last urinary output entry that was in or above the target range and comparing the time stamp for that entry to the current time, starting a timer when the urinary output is below the target range, or starting a counter that is incremented based on the number of wait delay periods or fractions there of if shorten as occurs in illustrated 1360. If the predetermined time threshold has been exceeded, then the wait delay is set to a shorten period of time, 1360. If the time threshold has not been exceeded or met, then the wait delay is set for the regular length, which is illustrated as 1 hour in 1375. After the wait delay is set, then the next infusion rate is calculated, 1365. In at least one embodiment, the processor starts a countdown timer that will alarm when the timer reaches zero to alert the medical staff that it is time to perform a check of the instruments. In another embodiment, at the end of the timer, the processor pulls (or receives) the necessary data from the infusion pump and urine meter. In yet another embodiment implemented on a portable system with limited battery power such as a PDA, the system hibernates (or other lowering of power consumption) between entry of at least one of the urinary output and infusion rate information and normalizes the numbers to the requisite wait time for calculating the new infusion rate, 1365.

If in 1335, it is determined that the urinary output is not below the target range, then it is determined whether a high output time threshold has been exceeded, 1380. In FIG. 13, the high output time threshold is illustrated as 3 hours. As discussed above, there are a variety of ways that can be used to track or determine the length of time. If the high output time threshold is not exceeded, then the wait delay is set for a regular wait time, which is illustrated as being 1 hour, 1385. If the high output time threshold has been exceeded, then the wait time is set for a shorten length, which is illustrated as 30 minutes, 1390. A reason for a shorten time period for the wait length is to provide for more frequent adjustment of the infusion rate to attempt to more rapidly bring the urinary output back into the urinary output target range. After the wait times are set, a new infusion rate is calculated, 1365, before repeating the process.

An alternative embodiment allows for the medical staff to terminate the process if the patient stabilizes during the resuscitation. The system upon receiving such a notification would terminate and treat the notification like an interrupt.

Another alternative embodiment would add an infusion rate condition to the determinations associated with the problem threshold and low output time threshold. The condition would require that the infusion rate was above a current infusion threshold in addition to the other condition. The infusion rate could be time sensitive in that it decreases over the resuscitation period. An example of the decrease would be that for each sixteen hour period the infusion rate would decrease. Examples for the current infusion thresholds are 500 mL for the first twelve hours, 300 mL for the next twenty-two hours, and 150 mL for the last fourteen hours. Although the infusion rate could be decreased linearly, exponentially or with any decay equation.

FIG. 14 illustrates another embodiment according to the invention for provide decision support for conducting a resuscitation of a burn patient. The method illustrated in FIG. 14 begins with receiving patient data including an estimate of the burn size and approximate weight for the patient, 1405. An additional parameter that may be received is the time of the burn injury or the approximate number of hours since the burn injury. Based on the received parameters, calculating a TBSA modifier ($Y_{TBSA}$) and a weight modifier ($Y_{weight}$), 1410.

The illustrated method then waits for a predetermined period of time before proceeding, 1415. The illustrated wait time is 1 hour although as discussed above other time lengths can be used. Alternatively, the wait delay for the first time through the method may be shorter to provide an initial urinary output and to allow for the infusion rate to be set to reflect the patient's condition. The urinary output is obtained, 1420.

The method in FIG. 14 further includes an error check relating to system failure or the patient being non-responsive to the resuscitation. After the urinary output is measured, determining whether the urinary output is below a problem threshold, 1421. The problem threshold is illustrated in FIG. 14 as being 5 mL/hr. If the urinary output is low, then notifying the medical staff of the potential problem, 1422. Receiving further instructions from the medical staff regarding whether the resuscitation should continue, 1423. If the resuscitation is to end, then stopping the method, 1424. If the resuscitation is to continue, then measuring the urinary output again, 1420. If the urinary output is above the problem threshold, then continuing to check the urinary output against additional thresholds in FIG. 14.

A determination is made as to whether the urinary output is below a non-response threshold, 1425. The non-response threshold is illustrated in FIG. 14 as being 15 mL/hr. Alternatively, this determination can also require that the current infusion rate be above a current infusion threshold as discussed above. If this determination is positive, then notifying the medical staff that the patient may be non-responsive and an intervention may be required, 1430. Receiving continuation instructions from the medical staff, 1435. Proceeding based on the continuation instructions, 1440. If the continuation instructions are to end, then the process is ended, 1424. If the continuation instructions are to proceed, then the new infusion rate is determined, 1450.

If the urinary output is in excess of the non-response threshold, then determining whether the urinary output is below a target range for a low time threshold, 1445. Alternatively, this determination can also require that the current infusion rate be above a current infusion threshold as discussed above. If this determination is positive, then notifying the medical staff that the patient may be non-responsive and an intervention may be required, 1430. Receiving continuation instructions from the medical staff, 1435. Proceeding based on the continuation instructions, 1440. If the continuation instructions are to end, then the process is ended, 1424. If the continuation instructions are to proceed, then the new infusion rate is determined, 1450.

If the urinary output is fine, then calculating a new infusion rate, 1450. As discussed above, there are a variety of ways according to the method for calculating an infusion rate. After the infusion rate is calculated, then waiting for a predetermined time before repeating the method, 1415. In at least one embodiment, the wait time is adjusted based on whether certain urinary output conditions have been met. For example, if any of the urinary output determinations are positive, then the method can set the wait time to a shortened time period.

An alternative embodiment illustrated in FIG. 14 sets the initial infusion rate for the resuscitation based on patient's weight and burn size area. Recognized infusion equations include the Brooke and Parkland infusion calculations in addition to the infusion equations discussed above.

Also illustrated in FIG. 14 is an alternative embodiment that includes a determination as to whether the patient has stabilized 1417 (although this determination could occur at any point in the method and act as an interrupt). The determination includes in at least one implementation receiving a notification from the medical staff that the patient has stabilized. In another implementation, the determination is made by the system based on physiological readings for the patient.

Both of these implementations can be combined together. If the patient has stabilized, then ending the process, 1424.

Figure 15A:
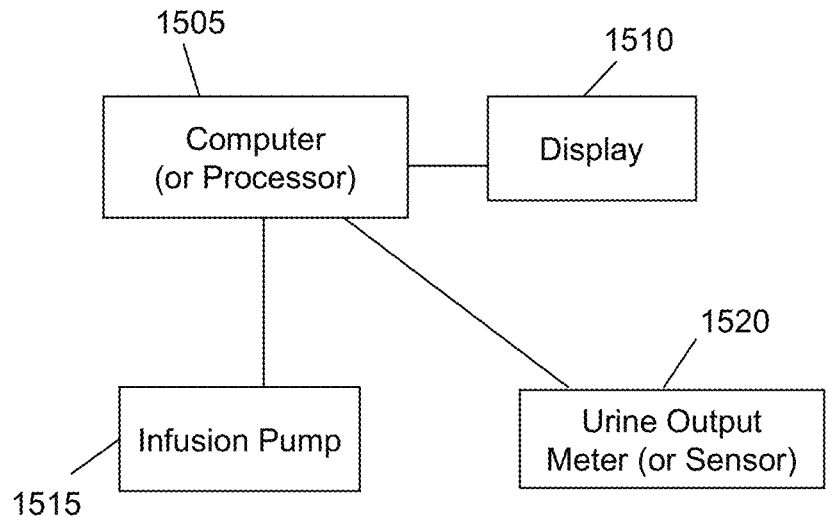
FIGS. 15A-15C illustrates a block diagram of a system according to the invention.

FIG. 15A illustrates a system that is able to perform the different methods described above. The illustrated system includes a computer (or other processing device such as a personal data assistance, tablet PC) 1505 with a display 1510 connected to an infusion pump 1515 such as an IV pump and a urinary output meter (or sensor) 1520 via serial connectors and/or analog-to-digital convertors. Communication between the different components of the system can occur through hardwire, wireless, or a combination. The computer 1505 can be continuous communication with the urinary output meter 1520 and/or the infusion pump 1515 collecting data for use in calculating new infusion rates.

Figure 15B:
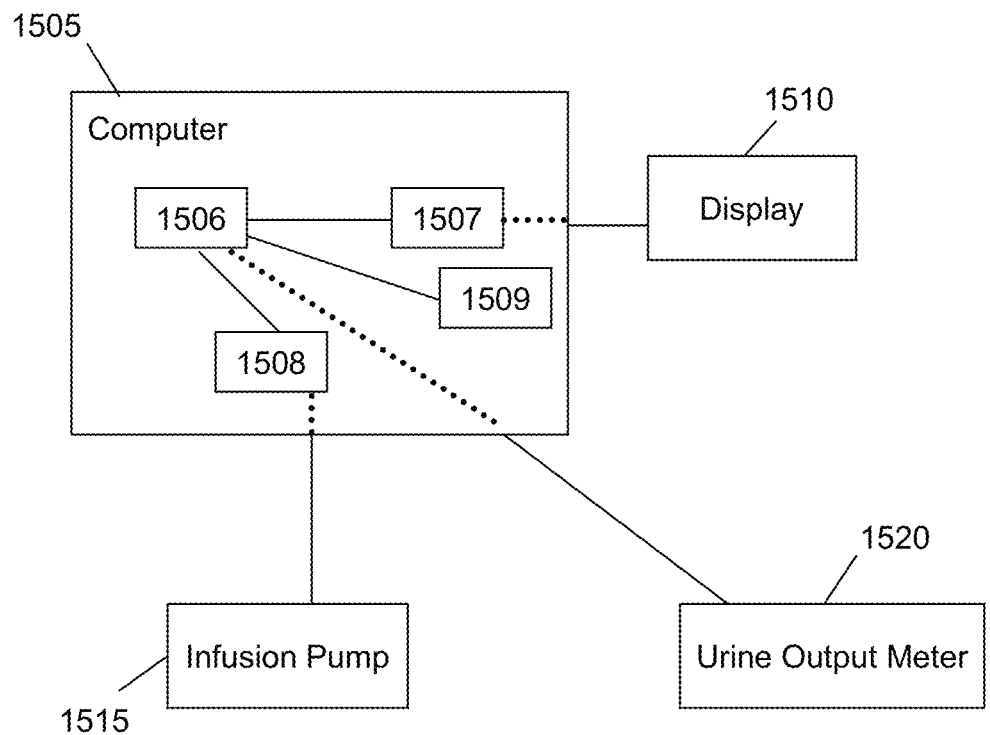

The computer or other processing means 1505 will include a variety of software and firmware for performing the above-described methods and to control the infusion pump according to the infusion rates determined by the system or received from the medical staff. In particular as illustrated in FIG. 15B, the computer 1505 will include calculating means 1506 for calculating an infusion rate in at least one of the manners described above, driving means 1507 for driving the display and receiving user entered information via the display, and controlling means 1508 for controlling the operation of the infusion pump 1515. In at least one embodiment, the computer 1505, the display 1510, and infusion pump 1515 are integrally built together thereby increasing the portability of the system.

Figure 15C:
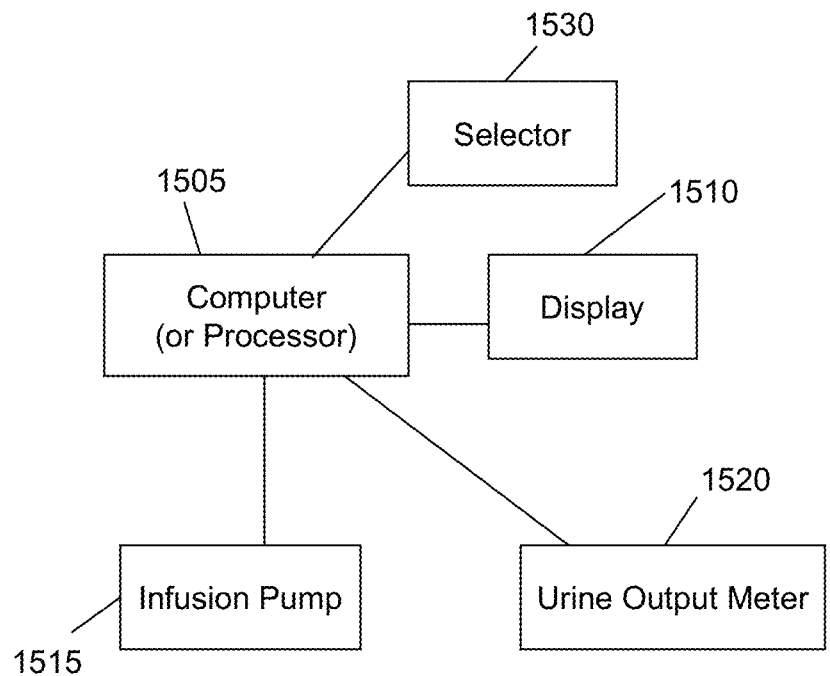

The system in at least one embodiment as illustrated in FIG. 15C includes a selector 1530 with at least two positions including a closed loop position and a semi-closed loop position that allows the user to select how the system operates. The selector 1530 is in communication with said computer 1505. Examples of the selector 1530 include, for example, a switch, slide device, a pair of push buttons, and a graphical interface element such as a virtual version of one of the mechanical selectors. FIG. 15C also illustrates an alternative embodiment that includes a notification means for notifying the medical staff when a problem has arisen, for example, with the system or the patient based on, for example, a communication glitch in the system or physiological data related to the patient has triggered a problem threshold as discussed above, for example, in connection with FIGS. 16A-16C.

In an implemented system, LabVIEW software is used for collection, management, control, and storage of digital, analog and multi-media data. Data retrieval and monitoring from instrumentation is stored in a synchronous fashion and can be monitored over a network (real time), stored in a database, retrieved for analysis as discrete digital information or for waveform analysis, and played back in its original captured form. In one implemented system, the system uses a FDA-approved infusion pumps (IMED Gemini PC-1, 2, 4) and a FDA-approved urine monitor (CritiCore, Bard Inc., Murray Hill, N.J.).

Automated fluid balance monitoring promotes an opportunity to generate displays of fluid balance, which in themselves may aid clinicians by rapidly imparting the time course of fluid balance. In at least one embodiment, hourly (or other time period) data is recorded for infusion rates, urinary output and net volume to be displayed graphically to illustrate any relationships between fluid therapy and urinary output for a particular period. An example of this type of display is FIG. 10E, which is a screen capture showing cumulative fluid in 1015C, urinary output 1020C, and net fluid (in minus urinary output) 1035C, measured with a prototype fluid balance monitor from data collected in an ovine model, consisting of 40% TBSA with acute respiratory distress syndrome (ARDS) secondary to inhalation injury. The display is generated from 34,560 data points, infusion rate, and urinary volume measured every 10 seconds for 48 hours. Per this experimental protocol, a steady infusion rate was set using the Parkland formula with adjustments only at 8- and 24-hr post-injury time points. Clearly evident are periods of oliguria 1020A at hours 28 through 35, despite continuous LR infusion at the Parkland rate. Also observed, as indicated with arrows ($\downarrow$), are the resolutions of net fluid accumulation 1035C first occurring transiently at 6-12 hours and then after 36 hours.

Another implemented version of a decision assist system uses manual hourly data input and provides hourly recommendations of infusion rate. One version of this system is built for tablet PCs for bedside use. Another version is written in JAVA code for implementation on USAISR standard clinical monitors. A mobile implementation of the software was written for use on a personal digital assistant (PDA) or smart phone that is field deployable and can be used in austere environments. The method can be implemented using a variety of software packages and/or computer languages.

Figure 16A:
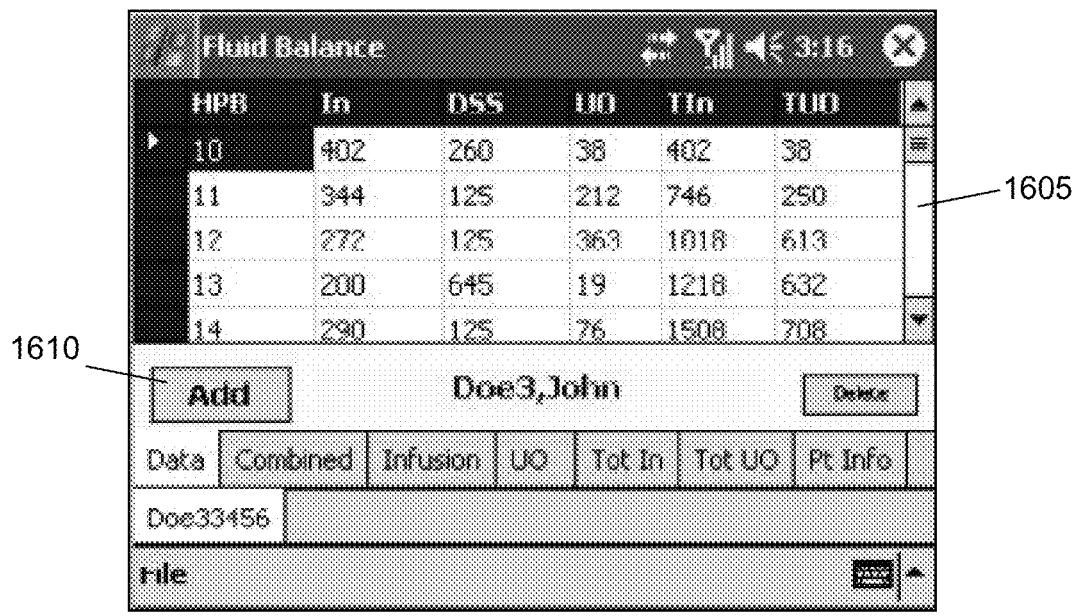
FIGS. 16A-16E illustrate together with FIGS. 10A and 10B an example set of interfaces according to the invention.
Figure 16B:
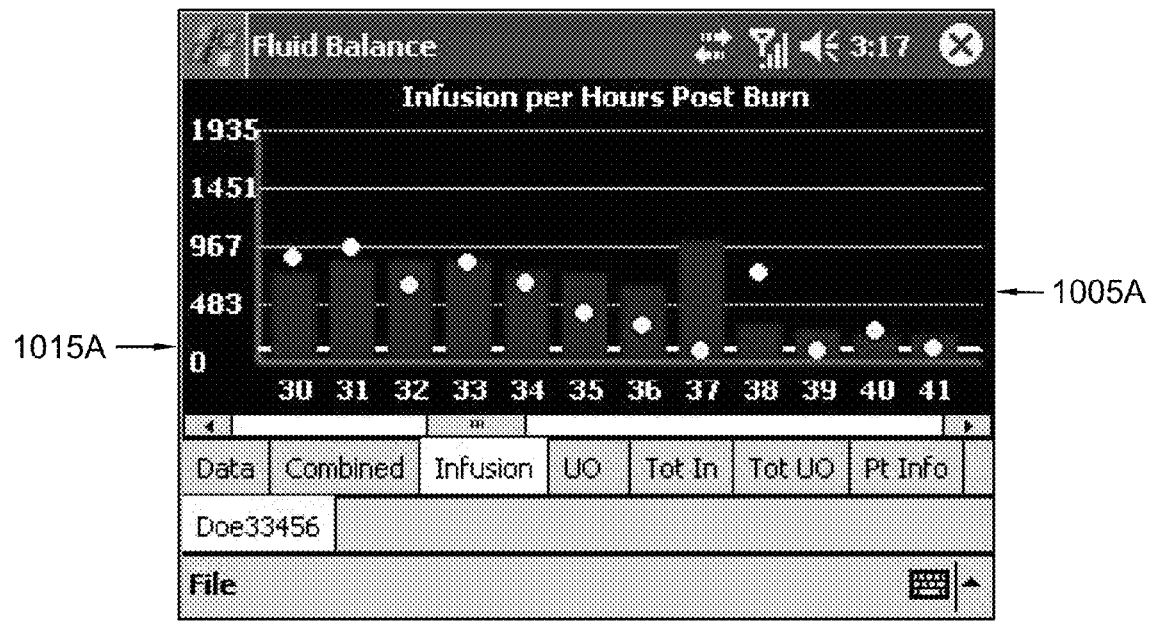
Figure 16C:
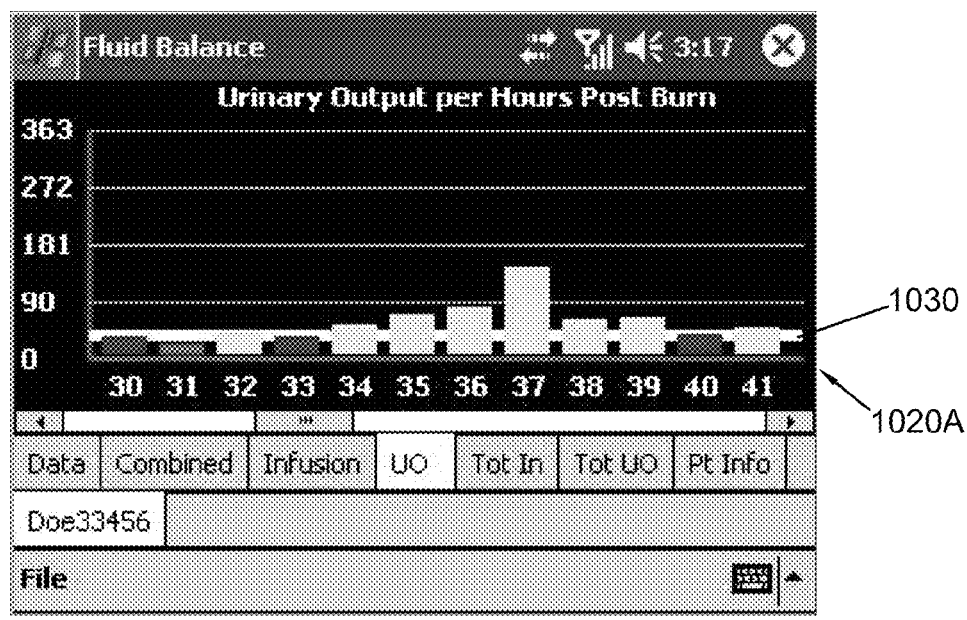
Figure 16D:
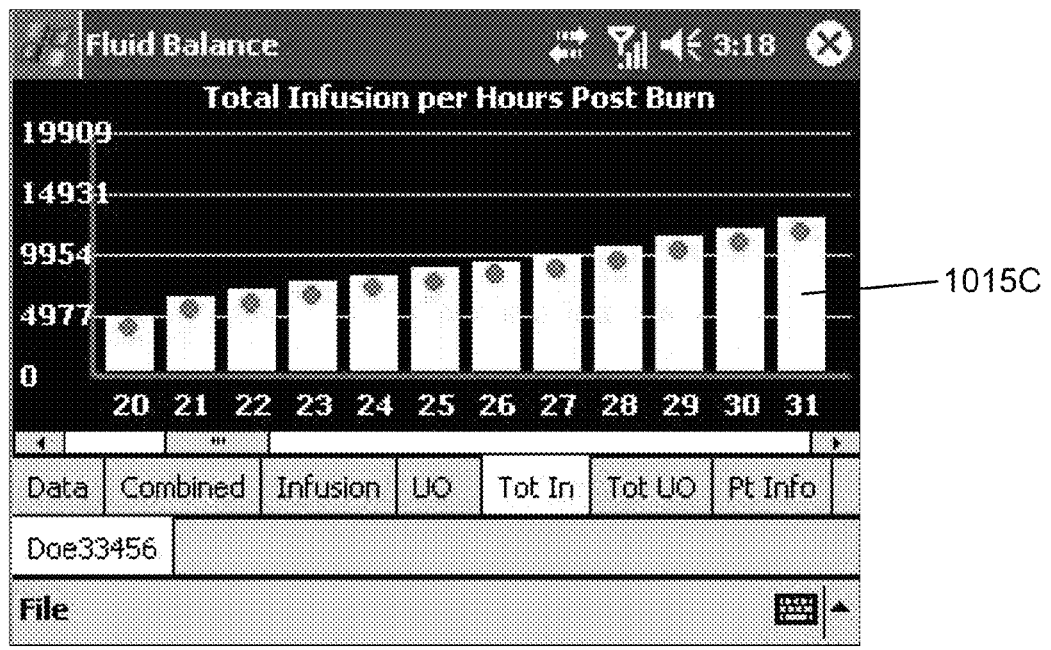
Figure 16E:
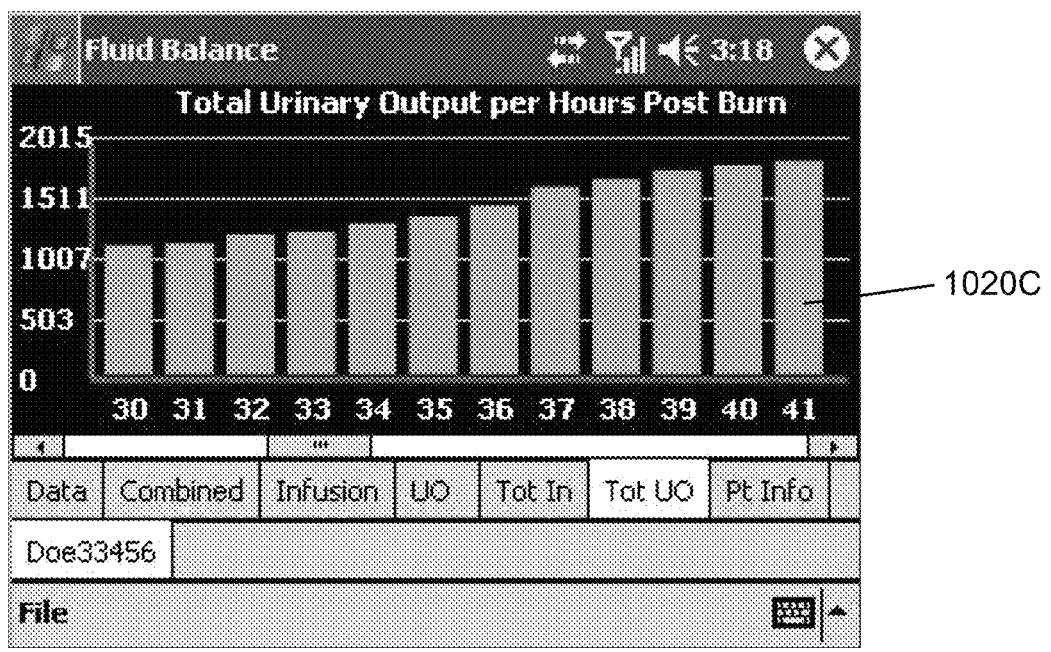

FIGS. 10A and 10B show two displays of the pocket PC fluid balance monitor with decision assist running. FIG. 10A illustrates a screenshot displaying infusion rates 1025A and urinary output 1020A for different hours during resuscitation with the recommended infusion rate 1005A being represented by the dots. The display in at least one embodiment will color code the urinary output to use one color to represent urinary output in range and one or more colors for when the urinary output is outside the target range. FIG. 10A illustrates an interface example for the medical staff to provide the infusion rate 1010 when the recommended infusion rate 1005 is changed and the urinary output and in response to the urinary output 1020 receive a recommendation for the infusion rate 1005 for the next time period. FIGS. 16A-16E illustrate different interface examples associated with FIGS. 10A and 10B that share a common tab arrangement for viewing different aspects and views of data collected by the system. FIG. 16A illustrates a data display screen that is illustrated as including hours post burn, infusion rate, DSS, urinary output (UO), cumulative infusion amount (Tin), and cumulative urinary output (TUO). The interface illustrated in FIG. 16A also allows the user to scroll 1605 through the data to look at desired data for particular hours and to add new data 1610. FIG. 16B illustrates an interface example for showing actual infusion rate (the bar graph) 1015A and recommend infusion rate (dots) 1005A versus time. FIG. 16C illustrates an interface example for showing urinary output 1020A versus time with a superimposed target range 1030. FIG. 16D illustrates an interface example for showing total infusion volume 1015C at each hour post burn, while FIG. 16E illustrates an interface example for showing total urinary output volume 1020C at each hour post burn.

Figure 17:
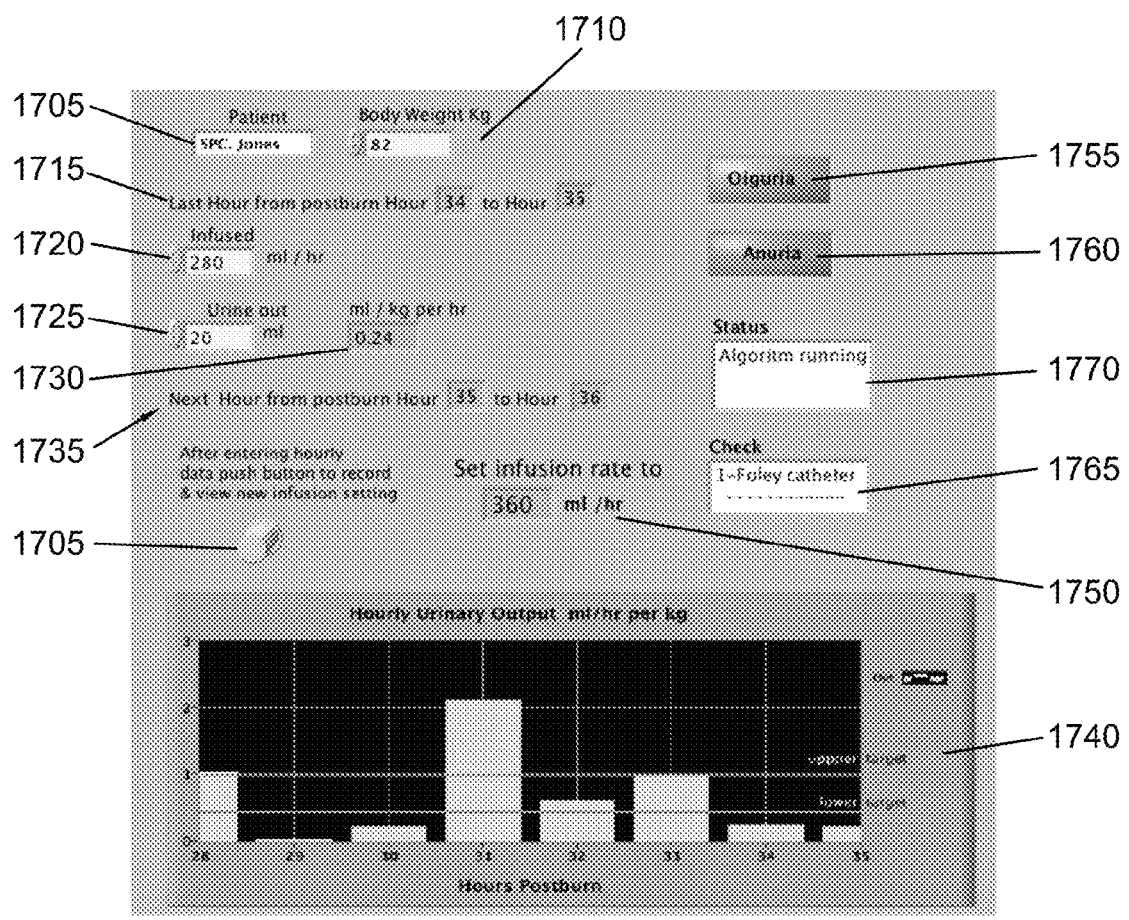
FIG. 17 illustrates an example interface according to the invention.
Figure 18:
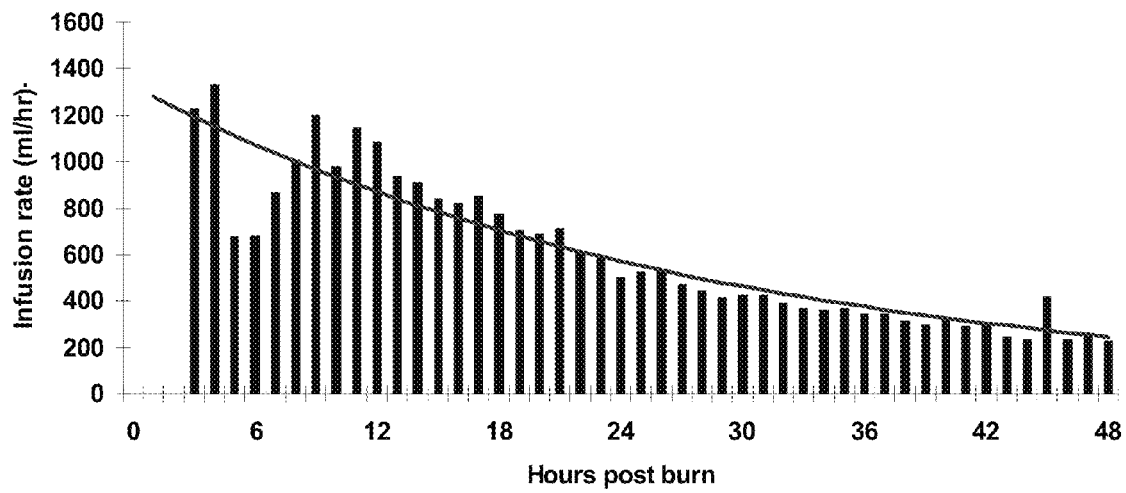
FIGS. 18-21 depict data supporting the invention.

FIG. 17 illustrates another interface example for use in a manual data entry implementation. The illustrated interface includes identification of the patient 1705, the patient's weight 1710, the last sampling period 1715, the infusion rate 1720, the urinary output in volume 1725 and converted to mL/kg 1730, identification of the next sampling period 1735, and a display area 1740. Both the infusion rate and urine out include arrow keys that can be used to adjust the value in the respective field if necessary. The display area 1740 can be used to display a variety of information as discussed above in connection with other figures even though the hourly urinary output is illustrated. The interface also includes an icon 1745 for obtaining the new infusion rate once the information for the last sampling period has been entered into the system. In an alternative embodiment, the icon 1745 could instead be used to accept the recommended infusion rate. The recommended infusion rate 1750 is display. The illustrated interface also includes examples of different warnings and alerts that can be provided including oiguria 1755, anuria 1760, recommendations of things to check 1765, and current status 1770. In at least one embodiment, the oiguria and anuria areas change color and/or brightness to indicate when those conditions exist.

The invention in at least one embodiment includes mechanisms for handling errors that may arise during use of the system. The system in at least one embodiment includes a robust data collection function with continuous data capture and display generation for 48 hours in several animal studies and up to 57 hours in patients. One main source of errors that can arise is when cables are disconnected or the urine monitor is not level. Errors generated by the system are classified into permanent or recoverable. Permanent errors entail the shutting off and re-initialization of the system. Recoverable errors are reported to the caregiver and logged by the system. In this case, the physician will decide whether to restart the system or to continue normal operation when recovered. A system of clinical alarms provides details to assist the caregiver in deciding when to disengage the system and initiate manual pump control. Error reduction algorithms can autocorrect for a variety of errors. For example, if the Bard urine collection canister is shaken, incorrect data changes in urine volume are transiently sent to the computer. Computer-generated alarms, notes, or comments are documented in the data record log and provided to the caregiver by popup windows. The current closed loop system version searches for devices to regain device connectivity. For example, when the connection is lost to the pump or urine monitor, an alarm and popup notifies the caregiver that the connection is lost. When the caregiver reattaches the connection, the data collection and algorithm resume. If either pump or urinary connectivity is lost for greater than five minutes an alarm notifies the caregiver to assume manual control and to restart the program manually.

When errors with connections arise, then in at least one embodiment, the systems will become decision-assist systems that allow for data to be manually entered by the medical staff and the system will provided a recommended infusion rate and other information as described above.

Research findings support that at least one embodiment of this invention will assist with resuscitation during the first 48 hours including providing fluid infusion recommendations based on a review of 30 burn patients admitted to the burn ICU at the U.S. Army Institute of Surgical Research burn unit and the University of Texas Medical Branch burn ICU.

Figure 19:
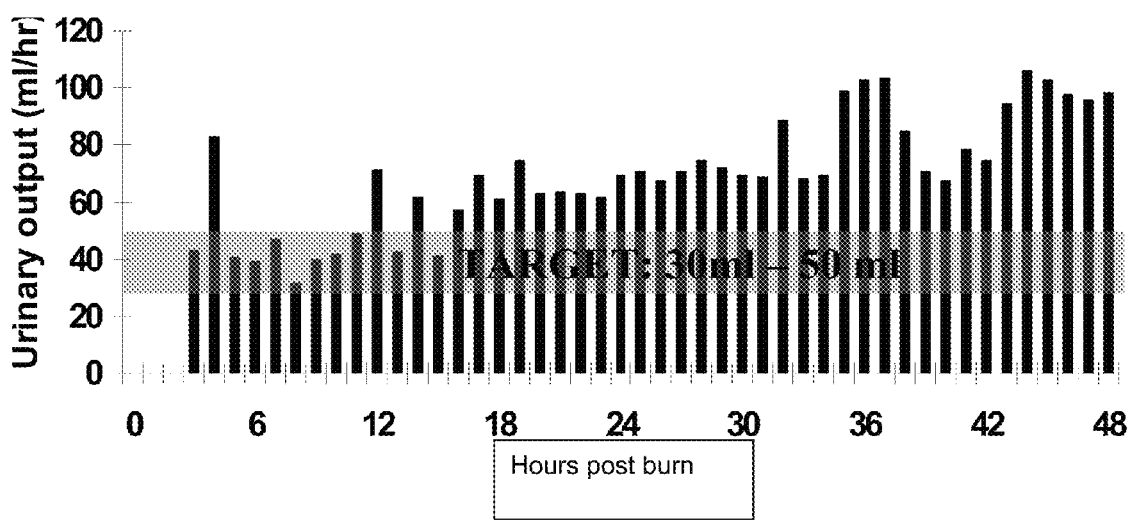
Figure 20:
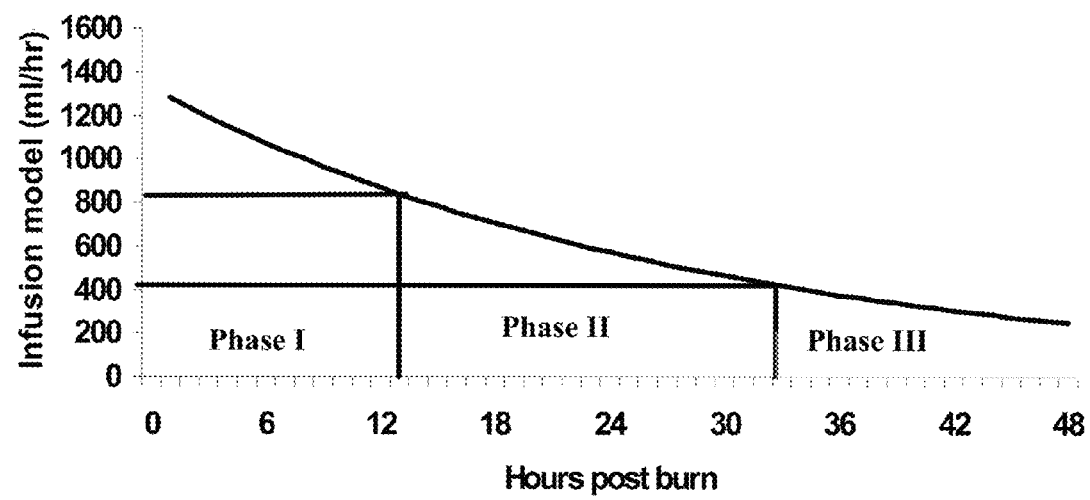
Figure 21:
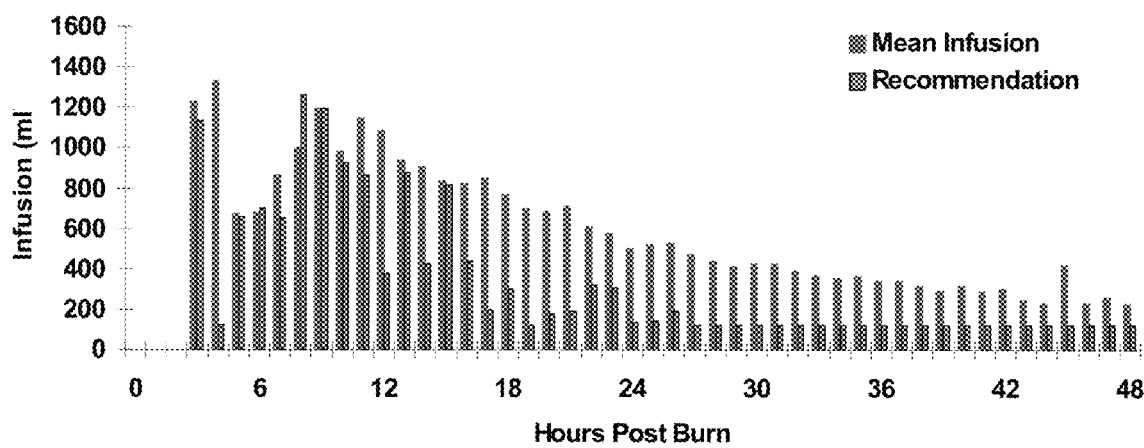

Patients with at least 20 percent total body surface area (TBSA) burn were considered for this study. Patients with electrical burns or who were intoxicated were excluded from this study. Fluid was initiated based on the standard Brooke (2 ml/kg/% TBSA over 24 hours) or Parkland (4 ml/kg/% TBSA over 24 hours) resuscitation formulas. Mean percentage of total body surface area was 39.8±21.4%. Mean age was 40±21 years. Infusion rate model was fitted using a decaying exponential curve as illustrated in FIG. 19. Mean expected urinary output or the first 48 hours is shown in FIG. 20. Based on mean urinary output values, on average patients are severely over resuscitated a majority of the time. The non-linear relationship between the infusion and urinary output was mitigated by subdividing the decaying curve into 3 distinct phases representing initial, middle, and end infusion phases illustrated in FIG. 21. In the initial phase (postburn hour 0-13) there is substantial variability between infusion rates and urinary outputs. Phase II (postburn hour 13-34) and phase III (postburn hour 34-48) algorithms are similarly designed and found to be sequentially less aggressive. Algorithm models an average infusion drop of 36 ml/hr for the first 13 hours, 23 ml/hr for hours 13 to 33, and 11 ml/hr for hours 33 to 48 with a corresponding urinary output increase of 1.2 ml/hr for all 48 hrs. Infusion requirements were then calculated using equation (1A):

$$I_t = I_{t-1} + e(t) \times \frac{IRC_t}{UOC_t} \tag{1A}$$

FIG. 22 illustrates the expected algorithm recommendations compared to the mean model values. Estimated algorithm recommendations resulted in a total fluid infusion of 55% below actual values for achieving an appropriate urinary output target.

The invention can take the form of an entirely hardware embodiment or an embodiment containing both hardware and software elements. In at least one exemplary embodiment, the invention is implemented in a system running software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium such as carrier signal. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Computer program code for carrying out operations of the present invention may be written in a variety of computer programming languages. The program code may be executed entirely on at least one computing device, as a stand-alone software package, or it may be executed partly on one computing device and partly on a remote computer. In the latter scenario, the remote computer may be connected directly to the one computing device via a LAN or a WAN (for example, Intranet), or the connection may be made indirectly through an external computer (for example, through the Internet, a secure network, a sneaker net, or some combination of these).

It will be understood that each block of the flowchart illustrations and block diagrams and combinations of those blocks can be implemented by computer program instructions and/or means. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowcharts or block diagrams.

The exemplary and alternative embodiments described above may be combined in a variety of ways with each other. Furthermore, the steps and number of the various steps illustrated in the figures may be adjusted from that shown.

It should be noted that the present invention may, however, be embodied in many different forms and should not be construed as limited to the embodiments set forth herein; rather, the embodiments set forth herein are provided so that the disclosure will be thorough and complete, and will fully convey the scope of the invention to those skilled in the art. The accompanying drawings illustrate exemplary embodiments of the invention.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

VI. INDUSTRIAL APPLICABILITY

The invention has industrial applicability to assist in the resuscitation of injured individuals who have received burns. The invention brings expertise out of the expert burn centers to medical staffs that may have no expertise and thus the care level provided by those medical staffs to patients should improve. The semi-closed loop system and the closed loop system are both useable in caring for burn patients when the medical staff does not have a sufficient level of experience and/or background to care for the burn patient, particularly during transport to a burn center.

VII. GLOSSARY

ABA—American Burn Association
ABLS—Advanced Burn Life Support
HPB—Hours Post Burn
LR—lactated Ringer's solution
PID—proportional-integral-derivative
TBSA—Total Body Surface Area
% TBSA—percentage Total body surface area
UO—Urinary Output
USAISR—U.S. Army Institute of Surgical Research
UTMB—University of Texas Medical Branch

We claim:

1. A system for use in resuscitating a patient comprising:
a urine sensor;
an infusion pump;
an electronic medical records interface; and
a processor connected to said urine sensor and said infusion pump, said processor having
means for calculating an infusion rate using an infusion rate model based on at least a current infusion rate received from at least one of said infusion pump and said electronic medical records interface, a current urinary output, and infusion rate model based constants, the new infusion rate is calculated using the following equation $$I_t = I_{t-1} + e(t) \times \frac{IRC_t}{UOC_t}$$

where $I_t$ is the new infusion rate, $I_{t-1}$ is the last infusion rate, e(t) is the urinary output error between the current urinary output and a target urinary output, $IRC_t$ is the infusion rate constant at time t based on the hours post burn, and $UOC_t$ is the urinary constant, and
wherein the urinary output error is further multiplied by a Gaussian function calculated using a mid-point of a target urinary output range.

2. The system according to claim 1, wherein the infusion rate constant decreases based on hours post-burn in at least two steps with a first step at 14 hours post burn and a second step at 34 hours post burn.

3. The system according to claim 1,
wherein the urinary output error is further multiplied by at least one of a modifier based on a patient's weight and a modifier based on a percentage of a total body surface area burned; and
at least one of the patient's weight and the percentage of the total body surface area burned are obtained from said electronic records system.

4. The system according to claim 1, wherein the Gaussian function is calculated using $$G = 1 - Ae^{-(X-B)^2/C^2}$$

where A is set to 1; X is set to the current urinary output; B is set to the mid-point of the target urinary output range; and C is set to 5.

5. The system according to claim 1, further comprising a timer connected to said processor, said calculating means calculates a new infusion rate when said timer expires after running for a predetermined time.

6. The system according to claim 5, wherein the predetermined time is based on hours post burn.

7. The system according to claim 1, further comprising a display, and
said processor further includes
means for driving said display and receiving information from said display of information entered by a user including an infusion rate different than the infusion rate calculated, and
means for controlling operation of said infusion pump at one of the calculated infusion rate and the different infusion rate received from the user until a new infusion rate is received or calculated.

8. The system according to claim 7, wherein said calculating means sets an initial infusion rate for the patient based on a predetermined formula.

9. The system according to claim 1, further comprising means for notifying medical staff when a problem has arisen with at least one of the patient and the system.

10. A system for use in resuscitating a patient comprising:
a urine sensor;
an infusion pump;
an electronic medical records system;
a timer; and
a processor connected to said urine sensor, said infusion pump, and said timer, said processor having program code embodied therewith, the program code executable by said processor to
calculate an infusion rate in response to a signal from said timer and based on at least the current infusion rate received from at least one of said infusion pump and said electronic medical records system, the current urinary output received from at least one of said urine sensor and said electronic medical records system, infusion rate model based constants, a patient's weight received from said electronic medical records system, a percentage of total body surface area received from said electronic medical records system, and a Gaussian function centered on a target urinary output, and
wherein the current urinary output is based on at least one of a running average of recent urinary outputs and an extrapolated flow based on recent urinary outputs.

11. The system according to claim 1, wherein said urine sensor includes a drop rate sensor.

12. The system according to claim 10, wherein the current urinary output is based on a running average of recent urinary outputs.

13. The system according to claim 10, wherein the infusion rate model based constants include an infusion rate constant and a urinary output constant.

14. The system according to claim 10, further comprising a display, and
said processor further having program code embodied therewith, the program code executable by the processor to
drive said display and receiving information from said display of information entered by a user including an infusion rate different than the infusion rate calculated, and
control operation of said infusion pump at one of the calculated infusion rate and the different infusion rate received from the user until a new infusion rate is received or calculated.

15. The system according to claim 10, wherein calculating the infusion rate uses the following equation $$I_t = I_{t-1} + e(t) \times \frac{IRC_t}{UOC_t} \times Y_{weight} \times Y_{tbsa} \times G_{UO}$$

where $I_t$ is the new infusion rate, $I_{t-1}$ is the last infusion rate, e(t) is the urinary output error, $IRC_t$ is the infusion rate constant at time t based on the hours post burn, $UOC_t$ is the urinary constant, $Y_{weight}$ is a modifier based on the patient's weight, $Y_{tbsa}$ is a modifier based on the percentage of the total body surface area, and $G_{UO}$ is the Gaussian function based on the target urinary output.

16. The system according to claim 15, wherein the Gaussian function is calculated using a mid-point of a target urinary output range, where the Gaussian function is calculated using $$G = 1 - Ae^{-(X-B)^2/C^2}$$

where A is set to 1; X is set to the current urinary output; B is set to the mid-point of the target urinary output range; and C is set to 5.

17. The system according to claim 10, wherein calculating the infusion rate sets an initial infusion rate for the patient based on a predetermined formula.

18. A system for use in resuscitating a patient comprising:
a urine sensor;
an infusion pump;
a display;
an electronic medical records system;
receiving means for receiving patient data including percentage of total body surface area burned and time since the patient was burned from said electronic medical records system;
first means for calculating an initial infusion rate based on at least the received patient data based on a predetermined formula;
second means for calculating an urinary output error based on a difference between a target urinary output and a current urinary output provided by at least one of said urine sensor and said electronic medical records system, and wherein the current urinary output is based on at least one of a running average of recent urinary outputs and an extrapolated flow based on recent urinary outputs;
third means for calculating a new infusion rate based on at least the calculated urinary output error multiplied by a constant calculated in part based on an exponential function with the input of hours post burn for the patient with the result being added to the current infusion rate;
outputting means for outputting the new infusion rate to at least one of said display, said electronic medical records system, and said infusion pump; and
a timer for controlling the operation of said second means, said third means and said outputting means.

19. The system according to claim 18, further comprising a processor having said receiving means, said first means, said second means, said third means, and said outputting means.

20. The system according to claim 18, wherein said third means calculates the infusion rate using the following equation $$I_t = I_{t-1} + e(t) \times \frac{IRC_t}{UOC_t} \times Y_{weight} \times Y_{tbsa} \times G_{UO}$$

where $I_t$ is the new infusion rate, $I_{t-1}$ is the last infusion rate, e(t) is the urinary output error, $IRC_t$ is the infusion rate constant at time t based on the hours post burn, $UOC_t$ is the urinary constant, $Y_{weight}$ is a modifier based on the patient's weight, $Y_{tbsa}$ is a modifier based on the percentage of the total body surface area, and $G_{UO}$ is the Gaussian function based on the target urinary output; and the Gaussian function is calculated using a mid-point of a target urinary output range, where the Gaussian function is calculated using $$G = 1 - Ae^{-(X-B)^2/C^2}$$

where A is set to 1; X is set to the current urinary output; B is set to the mid-point of the target urinary output range; and C is set to 5.

* * * * *